(12) United States Patent
Colman

(10) Patent No.: US 8,985,639 B2
(45) Date of Patent: *Mar. 24, 2015

(54) LUER CONNECTORS

(71) Applicant: Oridion Medical 1987 Ltd., Jerusalem (IL)

(72) Inventor: Joshua Lewis Colman, Jerusalem (IL)

(73) Assignee: Oridion Medical 1987 Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/982,682

(22) PCT Filed: Dec. 12, 2012

(86) PCT No.: PCT/IL2012/050520
§ 371 (c)(1),
(2) Date: Jul. 30, 2013

(87) PCT Pub. No.: WO2013/088439
PCT Pub. Date: Jun. 20, 2013

(65) Prior Publication Data
US 2014/0062082 A1    Mar. 6, 2014

Related U.S. Application Data

(60) Provisional application No. 61/569,822, filed on Dec. 13, 2011.

(51) Int. Cl.
*A61M 39/10* (2006.01)
*A61M 16/00* (2006.01)
(Continued)

(52) U.S. Cl.
CPC ... *A61M 16/0003* (2013.01); *A61M 2039/1038* (2013.01); *A61M 39/1011* (2013.01);
(Continued)

(58) Field of Classification Search
USPC .......... 285/93, 339, 341, 342, 343, 354, 390; 604/905
See application file for complete search history.

(56) References Cited

U.S. PATENT DOCUMENTS 1,474,905 A * 11/1923 Keszthelyi .................... 285/331
4,369,781 A *  1/1983 Gilson et al. .................. 604/905
(Continued)

FOREIGN PATENT DOCUMENTS

JP    H0337642 U    4/1991
JP    2001187990 A  7/2001
(Continued)

OTHER PUBLICATIONS

International Search Report & Written Opinion of the International Searching Authority Application No. PCT/IL2012/050520 Completed: Apr. 21, 2013; Mailing Date: Apr. 25, 2013 7 pages.

*Primary Examiner* — David E Bochna
(74) *Attorney, Agent, or Firm* — St. Onge Steward Johnston & Reens LLC

(57) ABSTRACT

Luer connector including a primary Luer male connector having a secondary female section extending from a top distal part of the primary Luer male connector back towards a proximal part thereof, the primary Luer male connector including a first inner fluid flow channel extending from a proximal end thereof to the secondary female section, the primary Luer male connector being configured to mate with a primary Luer female connector having a secondary male section including a second inner fluid flow channel.

17 Claims, 11 Drawing Sheets

(51) Int. Cl.
*A61B 5/08* (2006.01)
*F16L 37/244* (2006.01)
*G01N 1/22* (2006.01)
*F16L 21/00* (2006.01)

(52) U.S. Cl.
CPC .............. *A61B5/082* (2013.01); *F16L 37/244* (2013.01); *G01N 1/2205* (2013.01); *A61M 39/10* (2013.01); *A61M 2039/1022* (2013.01); *A61M 2039/1083* (2013.01); *A61M 2039/1088* (2013.01); *F16L 21/007* (2013.01)
USPC ....................................................... 285/332.1

(56) References Cited

U.S. PATENT DOCUMENTS

| | | | |
|---|---|---|---|
| 5,906,402 A * | 5/1999 | Simmons et al. | 285/354 |
| 5,914,033 A | 6/1999 | Carlsson | |
| 6,050,978 A * | 4/2000 | Orr et al. | 604/905 |
| 6,113,068 A * | 9/2000 | Ryan | 604/905 |
| 6,394,992 B1 * | 5/2002 | Sjoholm | 604/905 |
| 6,437,316 B1 | 8/2002 | Colman et al. | |
| 6,932,795 B2 * | 8/2005 | Lopez et al. | 604/256 |
| 7,060,047 B2 | 6/2006 | Lodi et al. | |
| 7,104,520 B2 * | 9/2006 | Leinsing et al. | 604/905 |
| 7,244,249 B2 * | 7/2007 | Leinsing et al. | 604/905 |
| 7,396,051 B2 * | 7/2008 | Baldwin et al. | 604/905 |
| 7,591,181 B2 * | 9/2009 | Ales et al. | 285/93 |
| 7,763,013 B2 * | 7/2010 | Baldwin et al. | 604/905 |
| 7,857,787 B2 | 12/2010 | Masters et al. | |
| 7,899,528 B2 | 3/2011 | Miller et al. | |
| 7,922,148 B2 * | 4/2011 | Walborn | 251/128 |
| 7,976,532 B2 * | 7/2011 | Kitani et al. | 604/905 |
| 8,355,753 B2 | 1/2013 | Bochenko et al. | |
| 8,385,972 B2 | 2/2013 | Bochenko et al. | |
| 8,439,404 B2 | 5/2013 | Anton et al. | |
| 8,746,745 B2 | 6/2014 | Colman | |
| 2008/0265191 A1 | 10/2008 | Walborn | |
| 2008/0284167 A1 | 11/2008 | Lim et al. | |
| 2010/0036329 A1 | 2/2010 | Razack | |

FOREIGN PATENT DOCUMENTS

| | | |
|---|---|---|
| JP | 2002159579 A | 6/2002 |
| JP | 2005287941 A1 | 10/2005 |
| JP | 2008521577 A | 6/2008 |
| JP | 4166852 B2 | 10/2008 |
| WO | 2006060688 A2 | 6/2006 |
| WO | 2008144513 A1 | 11/2008 |

* cited by examiner

LUER CONNECTORS

FIELD OF THE INVENTION

Embodiments of the invention are related to Luer connectors configured to provide essentially undisturbed gas flow and, with possible provisions, allow for activation of a gas analyzing device upon achieving conditions allowing essentially undisturbed gas flow and negligible leak.

BACKGROUND

The Luer Taper is a standardized system of small-scale fluid fittings used for making leak-free connections between a male-taper fitting and its mating female part on medical and laboratory instruments, including hypodermic syringe tips and needles or stopcocks and needles. Named after the 19th century German medical instrument maker Hermann Wulfing Luer, it originated as a 6% taper fitting for glass bottle stoppers. Key features of Luer Taper connectors are defined in the ISO 594 standards. It is also defined in the DIN and EN standard 1707:1996 and 20594-1:1993.

There are two varieties of Luer Taper connections: Luer-Lok and Luer-Slip. Luer-Lok fittings are securely joined by means of a tabbed hub on the female fitting which screws into threads in a sleeve on the male fitting. Luer-Slip fittings simply conform to Luer taper dimensions and are pressed together and held by friction (they have no threads). Luer components are manufactured either from metal or plastic and are available from many companies worldwide.

As mentioned above, the Luer connectors are defined in the ISO 594 standard. This standard like many is written by the International Organization for Standardization (ISO), the worldwide federation of national standards bodies (ISO member bodies).

In the 1990s concern grew in the federation regarding the proliferation of medical devices fitted with Luer connectors and the reports of patient death or injury arising from misconnections that resulted in the inappropriate delivery of enteral solutions, intrathecal medication or compressed gases. Concerns regarding the use of Luer connectors with enteral feeding tubes and gas sampling and gas delivery systems were raised with the European Committee for Standardization (CEN/BT) and the European Commission. In November 1997 the newly created CHeF steering group set up a Forum Task Group (FTG) to consider the problem. The FTG produced CEN Report CR 13825, which concluded that there is a problem arising from the use of a single connector design for a number of incompatible applications. In a coronary care unit there are as many as 40 connectors on the medical devices used with a single patient. Therefore it is not surprising that misconnections are made. Medical devices have for many years followed the established principle of "safety under single fault conditions". Simply stated this means that a single fault should not result in an unacceptable risk. This principle is embodied in the requirements of numerous medical device standards. Extending this principle to the application of Luer connectors, i.e. that misconnection should not result in an unacceptable risk to a patient the FTG recommended that Luer connectors should be restricted to medical devices intended to be connected to the vascular system or a hypodermic syringe. In addition, new designs of small-bore connectors should be developed for other applications, and these should be non-interconnectable with Luer connectors and each other.

In reaction to this defined need, during the past few years a new set of standards have been developed with the standard ISO/ICE 80369-(1); "Small-bore connectors for liquids and gases in healthcare applications" defining the general requirements for connectors used with fluids in the medical environment, where "Part 2" defines the specific connectors for "breathing systems and driving gases for respiratory use." This category includes connectors for Capnography, which is the monitoring of the concentration or partial pressure of $CO_2$ in respiratory cases.

In Part 2, the requirements for connectors used with breathing systems and driving gasses are provided including definition and dimensions of a recommended new connector for this purpose. In this document, the concept, shape and dimensions of the proposed connector fittings are similar to the original Luer connectors defined in ISO 594, but its dimensions are enlarged by some 30%, sufficiently in order that the newly proposed connector cannot be mated with its original version. The tapered Luer connector as defined in the original ISO 594 standard was retained for use with infusion systems only. In fact, a third connector design using the same concept and shape, but with smaller dimensions is defined for a third group of connectors intended for use with enteral applications. Again, the dimensions have been chosen so that inter-connectivity among different types of connectors is prevented.

Even in the era when ISO 594 was used to define Luer connectors for breathing systems, and consequently for Capnography applications, it was noted that the defined design for the Luer may not have been optimal for Capnography. Somewhat unique to Capnography, where accurate display of the CO2 waveform as created by ever changing inhalation and exhalation stages of breathing is necessary, major attention must be given to how the sampled breath is transferred from the patient to the measuring device. The sampling technique must ensure that the waveform fidelity and shape of the changing $CO_2$ concentration is kept by using very constant laminar flow with an undisturbed wave-front. Such disturbances are magnified if the gas flow passes via rough tubing, liquid filters, or sections of varying diameter in the tubing, conduits or connectors, abrupt changes in direction and irregularities etc. A measure of merit for the system ability to transfer the sampled breath from the patient to the measuring sensor of the Capnograph is the system Rise Time (sometimes referred to as the response time). A fast rise time is indicative of a well designed transfer of the sampled breath, while a slow rise time is indicative of a poor transfer of the breath suffering from the disturbing features defined above.

It is noted in Patent application No. US 2008/0284167; Low volume fittings: that the defined shape and dimensions dictated by the ISO 594 standard do not lend themselves to providing a fast rise time because of inevitable changes in the gas flow conduit diameter of the mating connectors. This is a result of the fact that a preferred diameter for the internal conduit used for transmitting the sampled gas is 1 mm, especially for a Capnograph that uses low gas sampling flow rates, e.g. 50 ml/min. This is further worsened by material choice, since the common material used for producing these connectors is plastic as it is more economic and appropriate for disposable components With plastic it is difficult to control tolerances of the 6% tapered cone, and these differences in tolerance dictate differences in the matching and final position of the two mated fittings. The problem can be seen in FIG. 1 (A, B and C), which shows Luer connectors according to the prior art. Luer connector 10 includes a 6% tapered Luer male connector 12 and Luer female connector 14 having an inner a 6% tapered cone. When the matched fittings (Luer male connector 12 and Luer female connector 14) are coupled, there still remains a conduit section of length E that may change because of the inherent tolerances that are inevitable when producing mass production, plastic parts, for example, between E min (FIG. 1A), E avg. (FIG. 1B) and E max (FIG. 1C). These E values are defined in the standard and must be maintained when manufacturing Luer connector. E max, for that matter, may be defined as the largest (worst) length of conduit that is formed between the Luer male connector and Luer female connector that is still acceptable by the standard.

This drawback is increased considerably with the new pending standard, ISO/CD 80369-1.2, where as mentioned, the new dimensions proposed are even larger, creating an even larger change in diameters and consequently distorting further the wave-front and producing an even slower rise time. Tests performed with Aluminum connectors representative of the maximum, mean and minimum tolerances (see Table 1 hereinbelow) as defined in the new standard have shown up to a 180 msec increase in rise time, meaning a much slower rise time. Such an increase would mean that requirements and performance parameters for rise time defined in Capnograph specifications will become non-compliant.

TABLE 1

Male and Female Aluminum Cones for Large Luer Connector Simulators Rise Time Tests:

| Parameters | Samples | | | Standard Luers |
|---|---|---|---|---|
| | Aluminium Cones | | | |
| Range | max | mean | Min | Mean |
| $L_{d.sp.int.}$, mm | 3.5 | 1.8 | ~0.0 | 2.3 |
| Response Time | $188_{\pm19}$ | $92_{\pm9}$ | $6_{\pm7}$ | $9_{\pm9}$ |

Tested Samples:
Aluminium Cones:

Male - min & max deviations (ID = 5.2).
Female - min & max deviations.
Standard Luer Locks:

Typical Male (ID = 4.0) and Female.
Symbols for given dimensions:

$L_{d.sp.int.}$ - Male to Female Cones distance internal dimensions.

TABLE 1-continued

Male and Female Aluminum Cones for Large Luer Connector Simulators Rise Time Tests:

Testing Conditions:

$Q_{sampl.}$ ~50 mL/min.
Amb.: 24° C.; 33%; 931 mBar.
Testing Device:

Capnosat Capnograph (tubing direct to sensor)
$(RT)_{Back.}$ ~45 mSec - minimum Rise Time background.

An attempted solution to this problem is provided in patent application No. US 2008/0284167; Low volume fittings. However, this approach cannot be used to solve the issue while still remaining compliant to the new standard: ISO/CD 80369-1.2. For example; see FIGS. 1D and 1E showing a Luer connector 100 as described in patent application: No. US 2008/0284167. It is proposed to increase the length of the 6% tapered Luer male connector 102, with an elastomeric material 106 that protrudes away from Luer male connector 102 by a distance F away from top 108 to a distal surface 110. As a result, when the matched fittings (Luer male connector 102 and Luer female connector 104) are coupled, elastomeric (soft) material 106 is squeezed from distance F to distance E and a reduced length of large diameter is accomplished and the extended elastomeric material would prevent the previously inevitable region of larger diameter conduit and thereby reducing it to a minimum. Such a solution is not permissible with the new standard, since the extended elastomeric section of the tapered male Luer, and its reducing diameter with length (6% taper) could easily be pushed into the female connector of a smaller sized Luer. As explained, three sized Luers with similar 6% tapered cones are expected to be introduced, but their sizes are such that when rigid materials as required are used, a larger size Luer cannot mate with a smaller defined size. This would not be the case with the proposed solution in the said application (US 2008/0284167).

To prevent such miss-connection, the new standard requirements dictate the use of rigid materials as well as an absolute dimension for the diameter of the male and female cone edge i.e. the diameter of the female side input edge and male inserting edge noted with the letter "d" for the male side and "D" for the female side. FIG. 2 shows such small-bore connector and its corresponding dimensions (summarized in Table 2 herein below) as appeared in standard ISO/ICE 80369-2.

TABLE 2

| | | | Dimension | | |
|---|---|---|---|---|---|
| Ref. | Designation | | Minimum | Nominal | Maximum |
| a: ISO/ICE 80369-2 - RESP-125 dimensions of male small-bore connector (dimensions are in mm unless otherwise indicated). | | | | | |
| a | Angle of taper (degrees) (6% taper nominal) | | 3.44° | 3.44° | 3.52° |
| b | Thread angle of male lock fitting | | 50° | 50.0° | 55° |
| d | Diameter at the tip of the male taper 6% | | 4.851 | 4.902 | 4.953 |
| e | Length of male taper | | 8.509 | 8.636 | 8.763 |
| f | Inner diameter at the tip of the male taper 6% | | 1.0 | 1.95 | 2.9 |
| h | Major diameter of internal thread of male lock fitting (diameter at thread root) | | 9.039 | 9.166 | 9.293 |
| j | Minor diameter of internal thread of male lock fitting (diameter at thread crest) | | 7.747 | 7.874 | 8.01 |
| k | Thread width of male lock fitting at root | | 1.06 | 1.19 | 1.32 |
| L | Length of taper engagement | | 5.08 | 5.08 | 5.70 |
| m | Width between thread flanks at root | | 1.22 | 1.350 | 1.48 |
| n | Width between thread flanks at crest | | 1.83 | 1.96 | 2.08 |

TABLE 2-continued

| Ref. | Designation | Minimum | Nominal | Maximum |
|---|---|---|---|---|
| o | Thread lead, (mm per 360° revolution) (Right-hand trapezoidal thread is double start, 5.1 mm per revolution) | 4.95 | 5.08 | 5.21 |
| p | Pitch on internal trapezoidal tread | 2.41 | 2.54 | 2.67 |
| q | Thread width of male lock fitting at crest | 0.46 | 0.58 | 0.71 |
| r | Projection of nozzle from collar | 2.16 | 2.29 | 2.41 |
| s | Thread length from collar end of male lock fitting | 7.5 | 7.6 | 7.8 |
| u | Inner diameter at the fluid lumen (recommended) | 2.40 | 2.55 | 2.70 |
| w | Width of majr projections | 13.4 | 13.5 | 13.8 |
| x | Angle of inner lumen taper of the male taper 6% | 1.80° | 2.00° | 2.20° |
| y | Inner diameter at the end of the male taper 6% | 2.58 | 2.71 | 2.84 |
| z | Length of inner lumen inside the male taper 6% (f to y) | 9.8 | 9.9 | 10.0 |
| | b: ISO/ICE 80369-2 - RESP-125 dimensions of female small-bore connector (dimensions are in mm unless otherwise indicated). | | | |
| A | Angle of female taper (6% taper nominal) | 3.35° | 3.44° | 3.44° |
| B | Thread angle of female lock fitting | 55.0° | 60.0° | 60.0° |
| D | Diameter at the open of the female taper 6% | 4.750 | 4.869 | 5.004 |
| E | Depth of female taper | 13.19 | 13.31 | 13.44 |
| H | Major diameter of external thread of female lock fitting (diameter at thread crest) | 8.92 | 9.04 | 9.17 |
| J | Minor diameter of external thread of female lock fitting (diameter at thread root) | 7.64 | 7.77 | 7.90 |
| K | Thread width of female lock fitting at crest | 1.12 | 1.24 | 1.37 |
| L | Length of taper engagement | 5.08 | 5.08 | 5.70 |
| M | Outside width of lock thread at crest | 1.17 | 1.30 | 1.42 |
| N | Outside width of lock thread at crest | 1.91 | 2.03 | 2.16 |
| O | Thread lead, (mm per 360° revolution) (Right-hand trapezoidal thread is double start, 5.1 mm per revolution) | 4.97 | 5.10 | 5.23 |
| P | Pitch of external trapezoidal tread | 2.37 | 2.50 | 2.63 |
| Q | Thread width of female lock fitting at root | 0.38 | 0.51 | 0.54 |
| S | Thread length from open end of the female taper 6% | 2.5 | 2.7 | 2.8 |
| U | Inner diameter at the fluid lumen (recommended) | 2.40 | 2.55 | 2.70 |
| W | Width of major projections | 11.4 | 11.6 | 11.7 |

NR—not restricted
Particularly, the diameter at the open end of the female taper 6% is defined as "D".
The diameter at the tip of the male taper 6% is defined as "d".

In addition to the issue of conduits with changing diameters that occur when connecting the Luer fittings that comply with the standard, and the slower rise times that they promote, a further issue with these type connectors, is that they may incur leaks that will introduce erroneously low $CO_2$ concentrations measurements because of dilution. This is found more so with the Luer lock version, i.e. the version where correct mating is realized by screwing the two mating fittings together firmly. In the hospital and emergence environment, the number of tasks required and the limited time available together with the state of emergency often create a situation where connectors are not mated securely and firmly. This results, as mentioned in even larger regions of increased diameters as well as, in some cases leaks with their negative effect on the readings. Though the user is required to feel the positive feedback received when the fittings are screwed on correctly, the conditions in the medical environment often do not lend themselves for the user to be sensitive to this feedback.

Hence there is an important need to find an economical means for structuring and mating two fittings for use with Capnograph monitors and their patient interfaces that comply with all the relevant ISO standards, and that incur only a negligible and minor increase in rise time and will provide a means for permitting gas flow between them only when this condition has been realized without the need for the user to control it.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, according to some embodiments, a Luer connector for use in a respiratory gas sampling and/or delivery tubing systems, the connector comprising a primary Luer male connector, having a form of a tapered cone, comprising a secondary female section extending from a top distal part of the primary Luer male connector back towards a proximal part thereof, wherein the primary Luer male connector comprises a first inner fluid flow channel extending along its length from a proximal end thereof to (and in fluid flow connection with) the secondary female section, wherein the first inner fluid flow channel has a diameter of approximately d1, wherein the diameter increases at a connection point between the first inner fluid flow channel and the secondary female section to form a neck N, wherein the internal diameter of the neck N is between d1 and d2, wherein the secondary female section has an internal diameter of d2 at a top distal part of the primary Luer male connector, wherein d1 is smaller than d2, wherein the primary Luer male connector is configured to mate with a primary Luer female connector having a form of a tapered cone, wherein at its deepest point, the tapered cone inverts back into a secondary male section and returns into a void of the primary Luer female connector, wherein the secondary male section comprises a second inner fluid flow channel extending along the length thereof and having an internal diameter of approximately d1, wherein when the primary Luer male connector and the primary Luer female connector mate with each other, the secondary male section is at least partially inserted into the secondary female section.

There is provided herein, according to some embodiments, a Luer connector for use in a respiratory gas sampling and/or delivery tubing systems, the connector comprising a primary Luer female connector having a form of a tapered cone, wherein at its deepest point, the tapered cone inverts back into a secondary male section and returns into a void of the primary Luer female connector, wherein the secondary male section comprises a second inner fluid flow channel extending along the length thereof and having an internal diameter of approximately d1, wherein the primary Luer female connector is configured to mate with a primary Luer male connector, having a form of a tapered cone, comprising a secondary female section extending from a top distal part of the primary Luer male connector back towards a proximal part thereof, wherein the primary Luer male connector comprises a first inner fluid flow channel extending along its length from a proximal end thereof to (and in fluid flow connection with) the secondary female section, wherein the first inner fluid flow channel has a diameter of approximately d1, wherein the diameter increases at a connection point between the first inner fluid flow channel and the secondary female section to form a neck N, wherein the internal diameter of the neck N is between d1 and d2, wherein the secondary female section has an internal diameter of d2 at a top distal part of the primary Luer male connector, wherein d1 is smaller than d2, wherein when the primary Luer male connector and the primary Luer female connector mate with each other, the secondary male section is at least partially inserted into the secondary female section.

According to some embodiments, the secondary male section has a length L, which is higher than E max, wherein E max is the maximal distance formed between the top distal part of primary Luer male connector and the deepest point of primary Luer female connector, when primary Luer male connector and primary Luer female connector are mated.

According to some embodiments, an inner part of the secondary female section comprises at least a portion having a cone shape. An inner part of the secondary female section may be tapered essentially from the neck N to the top distal part of the primary Luer male connector.

According to some embodiments, inner walls of the secondary female section are essentially parallel to inner walls of the first and/or the second inner fluid flow channels.

According to some embodiments, the secondary female section comprises threads on at least a portion of an inner side thereof configured to at least partially mate with the secondary male section comprising threads on at least a portion of an outer side thereof.

According to some embodiments, the secondary male section comprises one or more side slits to permit allowance for tolerance.

According to some embodiments, the secondary male section comprises at sealing tip on a top portion thereof.

According to some embodiments, inner walls of the secondary male section are essentially parallel to inner walls of the first and/or the second inner fluid flow channels.

According to some embodiments, the secondary female section comprises a first conducting element, wherein the first conducting element is configured to close a circuit with a second conducting element positioned on the secondary male section when the primary Luer female connector and the primary Luer male connector are correctly placed with respect to one another. The first conducting element may be a conducting ring located on an inner circumference of the secondary female section and the second conducting element may comprise electrode strips.

It is noted that a conducting element as referred to herein, may be replaced with any element (such as, but not limited to, an optical element, a magnetic element and an electric element, e.g., inductance, capacitance, resistance element or any combination thereof) that will allow closing of a loop (e.g., circuit) between a first and a second elements when the primary Luer female connector and the primary Luer male connector are correctly placed with respect to one another. Thus, for example, in case the primary Luer female connector and the primary Luer male connector are not correctly placed with respect to one another or are not matching parts (for example, not configured for gas sampling/delivery), the respiratory gas sampling (such as a capnograph) and/or gas delivery system will not be activated and/or an alert will be produced indicating that the connection between the primary Luer female connector and the primary Luer male connector is not correct/effective.

There is provided herein, according to some embodiments, a Luer connector for use in a respiratory gas sampling and/or delivery tubing systems, the connector comprising a primary Luer male connector, having a form of a tapered cone, comprising a secondary female section extending from a top distal part of the primary Luer male connector back towards a proximal part thereof, wherein the primary Luer male connector comprises a first inner fluid flow channel extending along its length from a proximal end thereof to (and in fluid flow connection with) the secondary female section, wherein the first inner fluid flow channel has a diameter of approximately d1, wherein the diameter increases at a connection point between the first inner fluid flow channel and the secondary female section to form a neck N, wherein the internal diameter of the neck N is between d1 and d2, wherein the secondary female section has an internal diameter of d2 at a top distal part of the primary Luer male connector, wherein d1 is smaller than d2, wherein the primary Luer male connector is configured to mate with a primary Luer female connector having a form of a tapered cone, having an opening at its deepest point, wherein a spring loaded insert is configured to be inserted through the opening essentially along a central axis of primary Luer female connector, wherein when the primary Luer male connector and the primary Luer female connector mate with each other, the spring loaded insert is at least partially inserted into the secondary female section.

There is provided herein, according to some embodiments, a Luer connector for use in a respiratory gas sampling and/or delivery tubing systems, the connector comprising a primary Luer female connector having a form of a tapered cone, having an opening at its deepest point, wherein a spring loaded insert is configured to be inserted through the opening essentially along a central axis of primary Luer female connector, wherein the primary Luer female connector is configured to mate with a primary Luer male connector, having a form of a tapered cone, comprising a secondary female section extending from a top distal part of the primary Luer male connector back towards a proximal part thereof, wherein the primary Luer male connector comprises a first inner fluid flow channel extending along its length from a proximal end thereof to (and in fluid flow connection with) the secondary female section, wherein the first inner fluid flow channel has a diameter of approximately d1, wherein the diameter increases at a connection point between the first inner fluid flow channel and the secondary female section to form a neck N, wherein the internal diameter of the neck N is between d1 and d2, wherein the secondary female section has an internal diameter of d2 at a top distal part of the primary Luer male connector, wherein d1 is smaller than d2, wherein when the primary Luer male connector and the primary Luer female connector mate with each other, the spring loaded insert is at least partially inserted into the secondary female section.

According to some embodiments, the spring loaded insert has a length L, which is higher than E max, wherein E max is the maximal distance formed between the top distal part of primary Luer male connector and the deepest point of primary Luer female connector, when primary Luer male connector and primary Luer female connector are mated.

According to some embodiments, inner walls of the secondary female section are essentially parallel to inner walls of the first and/or the second inner fluid flow channels. According to some embodiments, the inner walls of the secondary female section and the outer walls of the spring loaded insert are conical and adapted to fit each other.

According to some embodiments, the secondary female section comprises a first conducting element, wherein the first conducting element is configured to close a circuit with a second conducting element positioned on the spring loaded insert when the primary Luer female connector and the primary Luer male connector are correctly placed with respect to one another. The first conducting element may be a conducting ring located on an inner circumference of the secondary female section and the second conducting element may include electrode strips.

There is provided herein, according to some embodiments, a Luer connector for use in a respiratory gas sampling and/or delivery tubing systems, the connector comprising a primary Luer male connector, having a form of a tapered cone, comprising a secondary female section extending from a top distal part of the primary Luer male connector back towards a proximal part thereof, wherein the primary Luer male connector comprises a first inner fluid flow channel extending along its length from a proximal end thereof to (and in fluid flow connection with) the secondary female section, wherein the first inner fluid flow channel has a diameter of approximately d1, wherein the diameter increases at a connection point between the first inner fluid flow channel and the secondary female section to form a neck N, wherein the internal diameter of the neck N is between d1 and d2, wherein the secondary female section has an internal diameter of d2 at a top distal part of the primary Luer male connector, wherein d1 is smaller than d2, wherein the primary Luer male connector is configured to mate with a primary Luer female connector having a form of a tapered cone, wherein at its deepest point, the tapered cone inverts back into a secondary male section and returns into a void of said primary Luer female connector, wherein the secondary male section comprises a second inner fluid flow channel extending along the length thereof and having an internal diameter of approximately d1, wherein the primary Luer male connector comprises a first electric element, wherein the first electric element is configured to close a circuit with a second electric element positioned on the primary Luer female connector when the primary Luer female connector and the primary Luer male connector are correctly placed with respect to one another.

There is provided herein, according to some embodiments, a Luer connector for use in a respiratory gas sampling and/or delivery tubing systems, the connector comprising a primary Luer female connector having a form of a tapered cone, wherein at its deepest point, the tapered cone inverts back into a secondary male section and returns into a void of the primary Luer female connector, wherein the secondary male section comprises a second inner fluid flow channel extending along the length thereof and having an internal diameter of approximately d1, wherein the primary Luer female connector is configured to mate with a primary Luer male connector, having a form of a tapered cone, comprising a secondary female section extending from a top distal part of the primary Luer male connector back towards a proximal part thereof, wherein the primary Luer male connector comprises a first inner fluid flow channel extending along its length from a proximal end thereof to (and in fluid flow connection with) the secondary female section, wherein the first inner fluid flow channel has a diameter of approximately d1, wherein the diameter increases at a connection point between the first inner fluid flow channel and the secondary female section to form a neck N, wherein the internal diameter of the neck N is between d1 and d2, wherein the secondary female section has an internal diameter of d2 at a top distal part of the primary Luer male connector, wherein d1 is smaller than d2, wherein the primary Luer male connector comprises a first electric element, wherein the first electric element is configured to close a circuit with a second electric element positioned on the primary Luer female connector when the primary Luer female connector and the primary Luer male connector are correctly placed with respect to one another.

According to some embodiments, the secondary female section comprises the first electric element, and said secondary male section comprises said second electric element. The first and/or second electric elements may include a conducting, inductance, capacitance, resistance element or any combination thereof.

According to some embodiments, when the primary Luer male connector and the primary Luer female connector mate with each other, the secondary male section is at least partially inserted into the secondary female section.

There is provided herein, according to some embodiments, a Luer connector for use in a respiratory gas sampling and/or delivery tubing systems, the connector comprising a primary Luer male connector, having a form of a tapered cone, comprising a secondary female section extending from a top distal part of the primary Luer male connector back towards a proximal part thereof, wherein the primary Luer male connector comprises a first inner fluid flow channel extending along its length from a proximal end thereof to (and in fluid flow connection with) the secondary female section, wherein the first inner fluid flow channel has a diameter of approximately d1, wherein the diameter increases at a connection point between the first inner fluid flow channel and the secondary female section to form a neck N, wherein the internal diameter of the neck N is between d1 and d2, wherein the secondary female section has an internal diameter of d2 at a top distal part of the primary Luer male connector, wherein d1 is smaller than d2, wherein the primary Luer male connector is configured to mate with a primary Luer female connector having a form of a tapered cone, having an opening at its deepest point, wherein a spring loaded insert is configured to be inserted through the opening essentially along a central axis of primary Luer female connector, wherein the primary Luer male connector comprises a first electric element, wherein the first electric element is configured to close a circuit with a second electric element positioned on the primary Luer female connector when the primary Luer female connector and the primary Luer male connector are correctly placed with respect to one another.

There is provided herein, according to some embodiments, a Luer connector for use in a respiratory gas sampling and/or delivery tubing systems, the connector comprising a primary Luer female connector having a form of a tapered cone, having an opening at its deepest point, wherein a spring loaded insert is configured to be inserted through the opening essentially along a central axis of primary Luer female connector, wherein the primary Luer female connector is configured to mate with a primary Luer male connector, having a form of a tapered cone, comprising a secondary female section extending from a top distal part of the primary Luer male connector back towards a proximal part thereof, wherein the primary Luer male connector comprises a first inner fluid flow channel extending along its length from a proximal end thereof to (and in fluid flow connection with) the secondary female section, wherein the first inner fluid flow channel has a diameter of approximately d1, wherein the diameter increases at a connection point between the first inner fluid flow channel and the secondary female section to form a neck N, wherein the internal diameter of the neck N is between d1 and d2, wherein the secondary female section has an internal diameter of d2 at a top distal part of the primary Luer male connector, wherein d1 is smaller than d2, wherein the primary Luer male connector comprises a first electric element, wherein the first electric element is configured to close a circuit with a second electric element positioned on the primary Luer female connector when the primary Luer female connector and the primary Luer male connector are correctly placed with respect to one another.

According to some embodiments, the secondary female section comprises the first electric element, and the spring loaded insert comprises the second electric element. The first and/or second electric elements may include a conducting, inductance, capacitance, resistance element or any combination thereof.

According to some embodiments, when the primary Luer male connector and the primary Luer female connector mate with each other, the spring loaded insert is at least partially inserted into the secondary female section.

There is provided herein, according to some embodiments, a Luer connector for use in a respiratory gas sampling and/or delivery tubing systems, the connector comprising a primary Luer male connector, having a form of a tapered cone, comprising a secondary female section extending from a top distal part of the primary Luer male connector back towards a proximal part thereof, wherein the primary Luer male connector comprises a first inner fluid flow channel extending along its length from a proximal end thereof to (and in fluid flow connection with) the secondary female section, wherein the first inner fluid flow channel has a diameter of approximately d1, wherein the diameter increases at a connection point between the first inner fluid flow channel and the secondary female section to form a neck N, wherein the internal diameter of the neck N is between d1 and d2, wherein the secondary female section has an internal diameter of d2 at a top distal part of the primary Luer male connector, wherein d1 is smaller than d2; and a primary Luer female connector having a form of a tapered cone, wherein at its deepest point, the tapered cone inverts back into a secondary male section and returns into a void of the primary Luer female connector, wherein the secondary male section comprises a second inner fluid flow channel extending along the length thereof and having an internal diameter of approximately d1, wherein when the primary Luer male connector and the primary Luer female connector mate with each other, the secondary male section is at least partially inserted into the secondary female section.

According to some embodiments, the secondary male section has a length L, which is higher than E max, wherein E max is the maximal distance formed between the top distal part of primary Luer male connector and the deepest point of primary Luer female connector, when primary Luer male connector and primary Luer female connector are mated.

There is provided herein, according to some embodiments, a Luer connector for use in a respiratory gas sampling and/or delivery tubing systems, the connector comprising a primary Luer male connector, having a form of a tapered cone, comprising a secondary female section extending from a top distal part of the primary Luer male connector back towards a proximal part thereof, wherein the primary Luer male connector comprises a first inner fluid flow channel extending along its length from a proximal end thereof to (and in fluid flow connection with) the secondary female section, wherein said first inner fluid flow channel has a diameter of approximately d1, wherein the diameter increases at a connection point between said first inner fluid flow channel and said secondary female section to form a neck N, wherein the internal diameter of the neck N is between d1 and d2, wherein the secondary female section has an internal diameter of d2 at a top distal part of the primary Luer male connector, wherein d1 is smaller than d2; and a primary Luer female connector having a form of a tapered cone, having an opening at its deepest point, wherein a spring loaded insert is configured to be inserted through the opening essentially along a central axis of primary Luer female connector, wherein when the primary Luer male connector and the primary Luer female connector mate with each other, the spring loaded insert is at least partially inserted into the secondary female section.

According to some embodiments, the spring loaded insert has a length L, which is higher than E max, wherein E max is the maximal distance formed between the top distal part of primary Luer male connector and the deepest point of primary Luer female connector, when primary Luer male connector and primary Luer female connector are mated.

According to some embodiments, any one of the connectors disclosed herein may be used in a gas analyzing device, such as, but not limited to, a capnograph.

There is provided herein, according to some embodiments, a filter housing for use in a respiratory gas sampling and/or delivery tubing systems comprising: a primary Luer male connector; wherein the primary Luer male connector comprises a secondary female section extending from a top distal part of said primary Luer male connector back towards a proximal part thereof, wherein the primary Luer male connector comprises a first inner fluid flow channel extending along its length from a proximal end thereof; a primary Luer female connector; wherein the primary Luer female connector at its deepest point, inverts back into a secondary male section, wherein the secondary male section comprises a second inner fluid flow channel extending along the length thereof; a filter adapted to absorb liquids; and at least one conducting strip.

According to some embodiments, the primary Luer female connector of the filter housing is adapted to be connected to a primary Luer male connector of a patient sampling tube and the primary Luer male connector of the filter housing is adapted to be connected to a primary Luer female connector of a monitor.

According to some embodiments, when the primary Luer female connector of the filter housing is connected to the primary Luer male connector of a patient sampling tube the secondary male section of the primary Luer female connector of the filter housing is at least partially inserted into a secondary female section of the primary Luer male connector of the patient sampling tube; and when the primary Luer male connector of the filter housing is connected to the primary Luer female connector of the monitor, a secondary male section of the primary Luer female connector of the monitor is at least partially inserted into the secondary female section of the primary Luer male connector of the filter housing.

According to some embodiments activation of the monitor occurs only when the entire sampling line is connected. According to some embodiments connecting the primary male Luer connector of the filter housing to the primary Luer female connector of the monitor will not actuate the monitor. According to some embodiments, the monitor is only actuated when the primary Luer female connector of the filter housing is correctly connected to the primary Luer male connector of the patient sampling tube and when the primary Luer male connector of the filter housing is correctly connected to the primary Luer female connector of the monitor.

According to some embodiments, the secondary female section of the primary Luer male connector of the filter housing comprises a first conducting element, and the secondary male section of the primary Luer female connector of the filter housing comprises a second conducting element.

According to some embodiments, the secondary male section of the primary Luer female connector of the monitor comprises a third conducting element. According to some embodiments, the secondary female section of the primary Luer male connector of the sampling tube comprises a fourth conducting element.

According to some embodiments, the first and second conducting elements comprise at least three receiving conductor pads, wherein each receiving conductor pad is separated from its neighboring conducting pad by a non-conducting gap. According to some embodiments first conducting element and second conducting elements are identical.

According to some embodiments the third conducting element (of the monitor) comprises at least two conducting strips separated by a non-conducting gap.

According to some embodiments the width of the gaps between the at least three receiving conductor pads of the first and second conducting elements is less than the width of the at least two conducting strips of the third conducting element (of the monitor).

According to some embodiments the fourth conducting elements (of the sampling tube) comprises a conducting ring.

According to some embodiments, only when the primary Luer male connector of the filter housing is correctly connected to the primary Luer female connector of the monitor, and when the primary Luer Female connector of the filter housing is correctly connected to the primary Luer male connector of the sampling tube an electric circuit is closed and the monitor is actuated. According to some embodiments, when the primary Luer male connector of the filter housing is connected to the primary Luer female connector of the monitor, but primary Luer male connector of the patient sampling tube is not connected to the primary Luer female connector of the filter housing, the monitor is not actuated.

According to some embodiments, the filter is a hollow fiber filter.

According to some embodiments, the filter housing further comprises a blocking element adapted to prevent exhaled air from circumventing said filter.

According to some embodiments, the filter is molded on the filter housing to prevent exhaled air from circumventing the filter.

According to some embodiments, the at least one conducting strip is adapted to conduct between the primary female Luer connector of the filter housing and the primary male connector of the filter housing.

According to some embodiments, the filter housing is configured to be incorporated into a respiratory gas sampling and/or delivery tubing systems.

There is provided herein, according to some embodiments, filter housing for use in a respiratory gas sampling and/or delivery tubing systems comprising:

a first primary Luer male connector; wherein the first primary Luer male connector comprises a secondary female section extending from a top distal part of the first primary Luer male connector back towards a proximal part thereof, wherein the first primary Luer male connector comprises a first inner fluid flow channel extending along its length from a proximal end thereof;

a second primary Luer male connector; wherein the second primary Luer male connector comprises a secondary female section extending from a top distal part of the second primary Luer male connector back towards a proximal part thereof, wherein the second primary Luer male connector comprises a first inner fluid flow channel extending along its length from a proximal end thereof;

a filter adapted to absorb liquids; and at least one conducting strip configured to conduct between the first primary male Luer connector and the second primary male connector.

According to some embodiments, the first primary Luer male connector of the filter housing is adapted to be connected to a primary Luer female connector of a patient sampling tube and the second primary Luer male connector of the filter housing is adapted to be connected to a primary Luer female connector of a monitor.

According to some embodiments, the secondary female section of the first primary Luer male connector of the filter housing comprises a first conducting element, and the secondary female section of the second primary Luer male connector of the filter housing comprises a second conducting element.

According to some embodiments, the first conducting element and the second conducting element comprise receiving conductor pads.

According to some embodiments, the secondary male section of the primary Luer female connector of the monitor further comprises a third conducting element. According to some embodiments, the third conducting element comprises electrode strips.

According to some embodiments, the secondary male section of the primary Luer female connector of the sampling tube, further comprises a fourth conducting element.

According to some embodiments, the monitor is only actuated when the first primary Luer male connector of the filter housing is connected to the primary Luer female connector of the patient sampling tube and when the second primary Luer male connector of the filter housing is connected to the primary Luer female connector of the monitor.

According to some embodiments, when the first primary Luer male connector of the filter housing is connected to the primary Luer female connector of the monitor, but primary Luer female connector of the patient sampling tube is not connected to the second primary Luer male connector of the filter housing, the monitor is not actuated.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

Figure 1A:
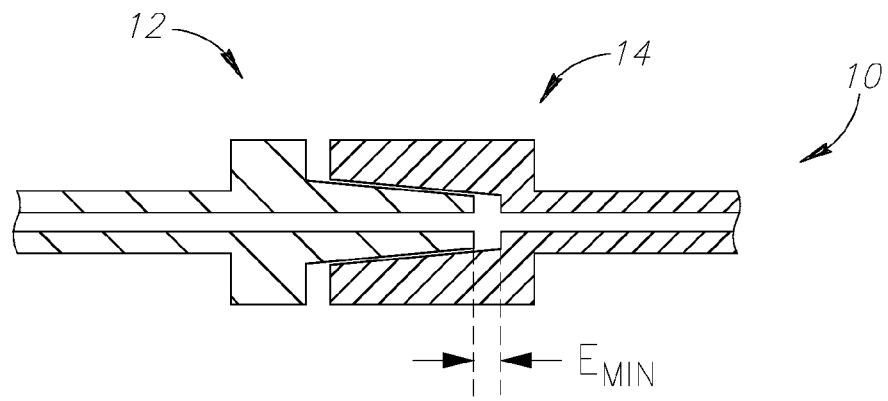
FIGS. 1A-E show a prior art Luer connector.
Figure 1B:
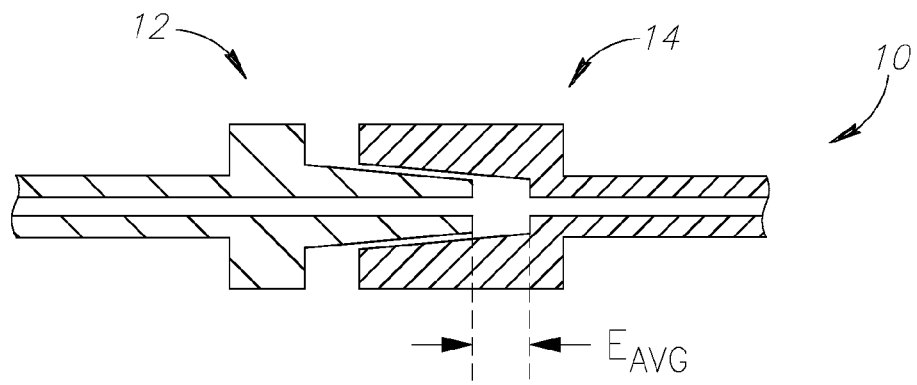

There is provided herein, according to some embodiments, a Luer connector, which includes a primary Luer male connector and a primary Luer female connector for use in gas tubing system. The Luer connectors, according to embodiments of the invention, may be used anywhere along a patient interface or sampling line. For example, the Luer connector, according to some embodiments, may be positioned at the monitor side between a monitor input connector and a patient interface. In another example, the Luer connector, according to some embodiments, may be positioned between an airway adaptor or a cannula and a sampling tube. The primary Luer male connector and the primary Luer female connector may be used interchangeably, for example, the primary Luer male connector may be used at the monitor (such as gas capnograph) side and the primary Luer female connector may be used at the (disposable) sampling line side, or vice versa, the primary Luer female connector may be used at the monitor (such as gas capnograph) side and the primary Luer male connector may be used at the (disposable) sampling line side.

According to some embodiment of the invention the proposed solutions includes at least one, though preferably two major features, primarily a mechanical structure that on one hand complies with the new standard ISO/CD 80369-2, but dictates that when the fittings are mated, the changes and jumps in diameter of the conduits within which the breath samples flow are reduced to a minimum, and this for a minimum length. Further, dictating minimal leak, even when both the male and female connectors are mated weakly. Secondly, according to some embodiments, the connector provides a simple means for detecting when minimal leak as well as minimal effect on rise time has been achieved and only then an automatic detection system activates the monitor sampling capability.

The following four main aspects of Luer connectors are presented as solutions, according to some embodiments, for the problems presented herein:

Luer Connector—First Aspect:

According to some embodiments, the first feature is accomplished by using a means comparable to optical systems where mechanical dimensions of an imaging system with long focal lengths dictate long optical paths. In such systems the optical paths are either folded upon themselves or redirected by mirrors in order to reduce the lengths of the total system. In a similar way, this folding principal is used with male and female Luer locks. As discussed, for optimal design with a Capnograph, the 6% tapered conical fitting would have preferably been increased in length so as to reach the point where the cone intersects the internal orifice of the internal conduit used for transmitting the breath sample. If this were the case, when the male and female Luer would have mated, theoretically there would have been only a negligible change in diameter when moving from the male to female connector and hence incurring negligible effect on the sampled breath rise time.

Such a design, even if it would have been acceptable with its extremely long connector, is unacceptable by definition in the said new standard, where the final (external) diameter at the end of the tapered connector is clearly limited to a diameter of 4.58 mm on the male side (defined by the letter "d") and 4.87 mm on the female side (defined by the letter "D") (see Table 1). To overcome this, while still complying with the above values for "d" and "D", it is possible to fold over the tapered cone, so that the male connector is extended in length by inverting the male extension into a female section which returns back into the male extension. The inversion is made when the (external) diameter of the male extension reaches the diameter "d", the nominal diameter as defined by the standard.

Figure 3A:
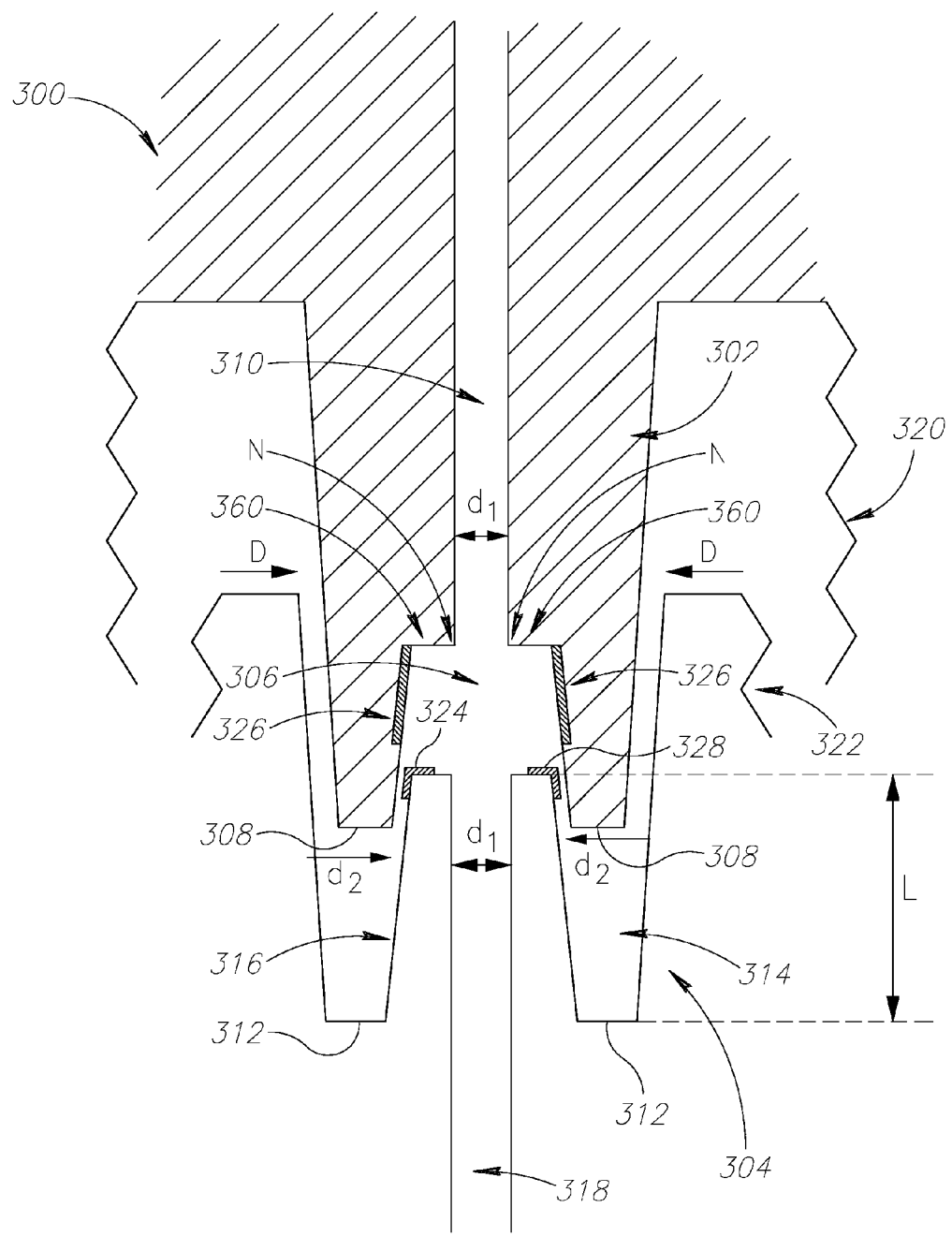
FIG. 3 show a cross section of a Luer connector, according to embodiments of the invention.

An example of a Luer connector having such inversion can be found in FIG. 3A, which shows a cross section of a Luer connector, according to embodiments of the invention. Luer connector 300 includes primary Luer male connector 302 and primary Luer female connector 304. Primary Luer male connector 302 includes female part which forms secondary female section 306 having a cone shape and extending from the top distal part 308 of primary Luer male connector 302 back into primary Luer male connector 302 towards the proximal part thereof. The primary Luer male connector 302 includes a (centralized) first inner fluid flow channel 310 extending along its length from a proximal end of primary Luer male connector 302 to (and in fluid flow connection with) secondary female section 306. First inner flow channel 310 has a diameter of d1. At a connection point between first inner fluid flow channel 310 and the secondary female section 306 the internal diameter is increased to form a neck N having surface 360 essentially perpendicular to the inner walls of first inner fluid flow channel 310, wherein the internal diameter of the neck N is between d1 and d2, wherein secondary female section 306 has an internal diameter of d2 at top distal part 308 of primary Luer male connector 302, wherein d1 is smaller than d2, According to another embodiment, not shown, the secondary female sections shown herein, for example but not limited to, secondary female section 306 may not be tapered. For example, secondary female section 306 may have an internal diameter of d2 at surface 360 and essentially the same internal diameter of d2 at top distal part 308 of primary Luer male connector 302. In other words, the internal walls of the secondary female section (such as secondary female section 306) may be essentially parallel to the internal walls of first or second inner fluid flow channels (such as first inner fluid flow channel 310).

Comparably, on the mating connector, primary Luer female connector 304, which is primarily female in shape, at its deepest point 312, the tapered cone 314 inverts back into a secondary male section 316, which has a cone shape and returns back into the void space of primary Luer female connector 304. The second inner fluid flow channel 318 extending along secondary male section 316 has a diameter of d1.

The diameter at the open end of primary Luer female connector (taper 6%) 304 is defined as "D".

The (external) diameter at the tip of the primary Luer male connector (taper 6%) 302 defined as "d".

In this manner, the two connectors (primary Luer male connector 302 and primary Luer female connector 304) still mate well, retain the dimensions "d" and "D" required by the standard but become more compact, and end with small diameters (d1) far less than "d" and "D", so that when gases flow from one to the other, minor changes in diameter are incurred and consequently reduce the effect on the rise time. In this manner, inadvertent insertion of a larger sized male Luer into a smaller sized female Luer is prevented as required by the new standard.

It is noted that for simplicity, the original part of the male and female Luer are called the primary male and female sections, while the inverted sections are referred to as the secondary male and female sections.

According to some embodiments, the secondary male and female sections (such as secondary male section 316 and secondary female section 306) have tapered angles whose tolerances are on the lower side of the tapered angle of the primary male and female sections (such as primary Luer male connector 302 and primary Luer female connector 304). This is in order that the two fittings do not close first on the shorter and smaller secondary male and female sections, but mate primarily with the primary male and female cones. It is also possible to produce the secondary male Luer section from a softer material than that used to make the secondary female section, where in this manner the secondary male section can be made of the same taper and its tolerances as the primary Luer. This addition of a soft material will still comply with the standard, since soft materials are disqualified from the design only for those regions where a dimension has been specified, and hence where the soft material will permit distortion and non-compliance of the required dimension.

According to some embodiments, an outer section of Luer connector 300 further includes screwing capability of one connector to its mating connector. Specifically, Luer male connector 302 includes threads 320 on an outer part thereof and primary Luer female connector 302 includes threads 322 on an outer part thereof.

It is noted that the Luer connectors, according to embodiment of the invention, can either be of normal Luer or of slip Luer, i.e. with external thread or without external thread, respectively.

According to some embodiments, when primary Luer male connector 302 and primary Luer female 304 mate with each other, secondary male section 316 is at least partially inserted to secondary female section 306.

Figure 1C:
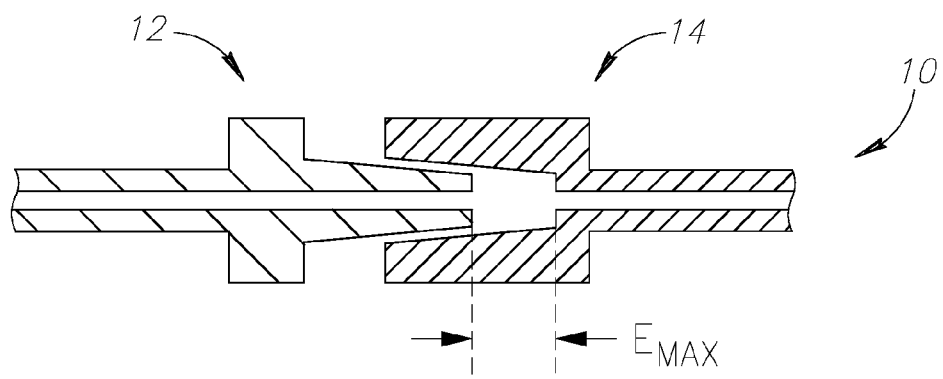
Figure 1D:
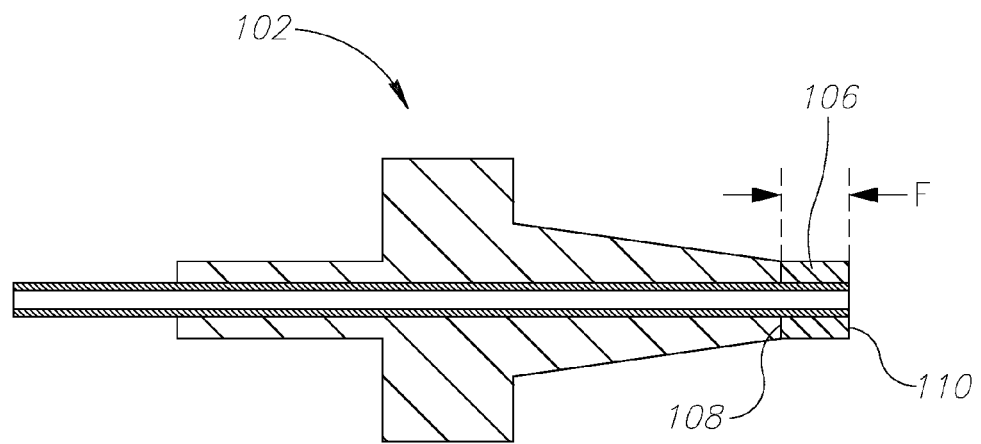
Figure 1E:
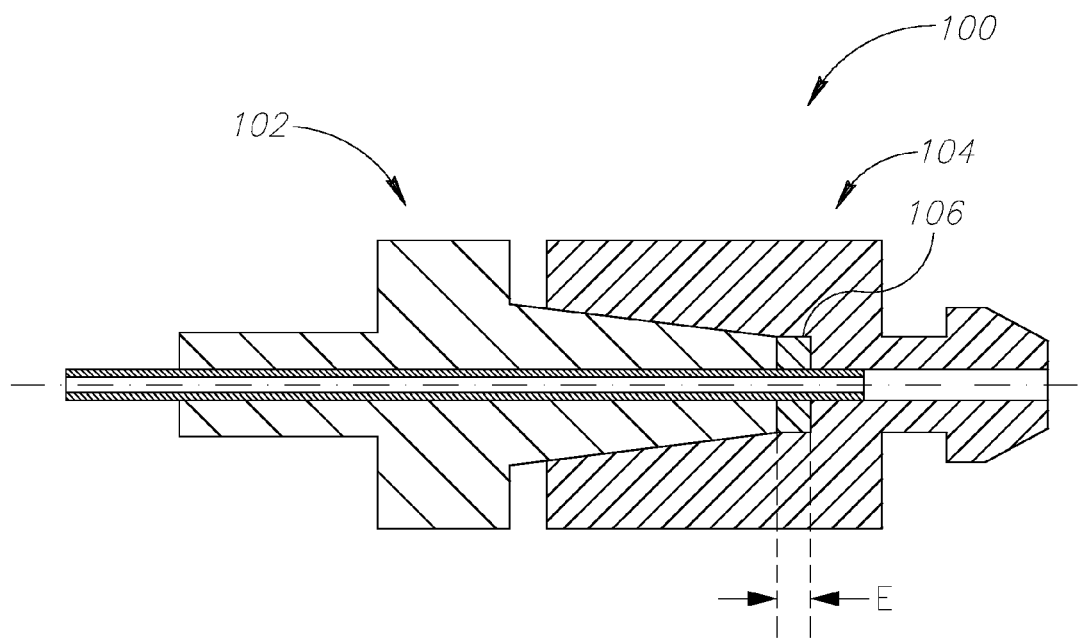
Figure 2:
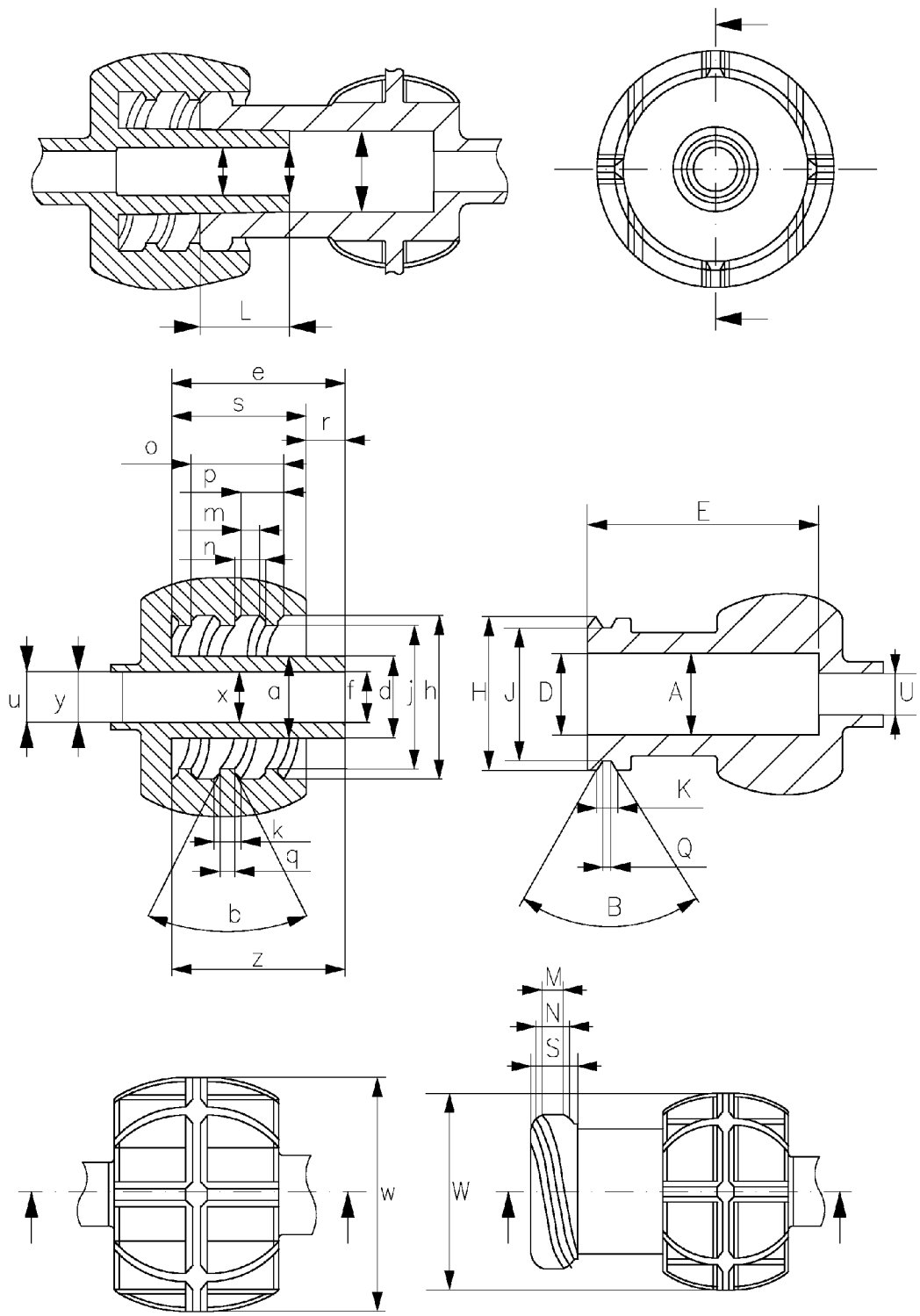
FIG. 2 shows a small-bore connector in accordance with standard ISO/ICE 80369-2.

According to some embodiments, secondary male section 316 has a length L, which is higher than E max, wherein E max is the maximal distance between top distal part 308 of primary Luer male connector 302 and deepest point 312 of primary Luer female connector 304, when primary Luer male connector 302 and primary Luer female connector 304 are mated and wherein the tolerances of their cones are at their limits (see for example FIG. 1C) and hence mating occurs early in the mating process.

The second feature, according to some embodiment, is used for detecting that the parts as designed above only actuates the monitor when minimal leaks and negligible changes in diameter have been realized. For this purpose, several methods can be used, for example, a method which is based on detecting changes to an electric circuit by either closing the circuit, changing its inductance or capacitance or the resistance in part of it, etc. Alternatively, a method which is based on detecting optical or magnetic changes can also be applied. For example, if on the monitor side, a primary female Luer lock is used, (two) electrode strips (for example 324 and 328) can line either the primary female opening (not shown) or secondary male section 316 to a point where when mating primary Luer male connector 302 is correctly placed it should reach this point of electrodes strips 324 and 328. On the mating primary Luer male connector 302, on the end thereof or internally at the end of secondary female section 306, a conducting ring 326 is placed. According to some embodiments, conducting ring 326 is positioned on the inner circumference of secondary female section 306. When the connectors are correctly and sufficiently in place, conducting ring 326 will close a circuit ending with electrode strips 324 and 328. Electrode strips 324 and 328 are, in turn connected to a circuit that can detect if there is conductance between the two or not, where on detection a signal is produced which consequently actuates the pump used to provide the sampling.

According to some embodiments, the term correctly placed as refers to herein, defines a mating between a primary Luer female connector and a primary Luer male connector where there is no significant deterioration or slowing of rise time, and where negligible leaking of sampled gas can occur.

Inductance or capacitance can also be used, or any other method which can change electronic characteristics of a circuit when two dielectric or conducting materials and surfaces are positioned one relevant to the other. The overlap of the two material surfaces may result from the correct mating of the connectors, or from reaching a distance between them which will change the electric characteristics proportionally to the level of mating between the two connectors. These changes can be detected by the monitor, actuating the monitor sampling system only when correct mating is achieved.

In a further embodiment, the conducting ring could vary in resistance, which when measured, can be used as an indicator for a given type or class monitor or type and class patient interface as ended with the relevant connector.

Figure 3B:
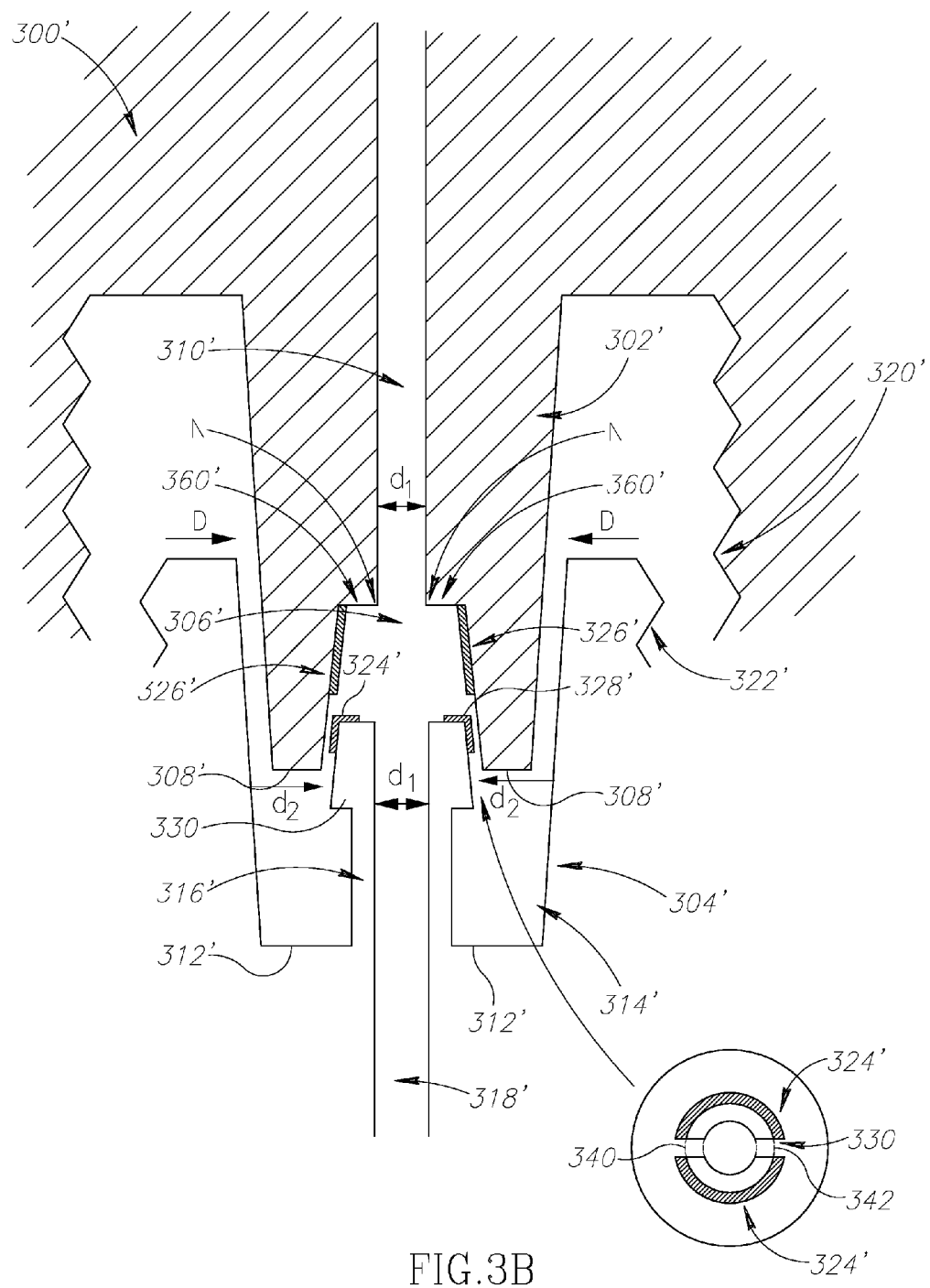

Another example of such inversion can be found in FIG. 3B, which shows a cross section of a Luer connector, according to embodiments of the invention. Luer connector 300' resembles Luer connector 300 of FIG. 3A excluding the structure of the secondary male section. Luer connector 300' includes primary Luer male connector 302' and primary Luer female connector 304'. Primary Luer male connector 302' includes female part which forms secondary female section 306' having a cone shape and extending from the top distal part 308' of primary Luer male connector 302' back into primary Luer male connector 302' towards the proximal part thereof. The primary Luer male connector 302' includes a (centralized) first inner fluid flow channel 310' extending along its length from a proximal end of primary Luer male connector 302' to (and in fluid flow connection with) secondary female section 306'. First inner channel 310' has a diameter of d1.

At a connection point between first inner fluid flow channel 310' and the secondary female section 306' the internal diameter is increased to form a neck N having surface 360' essentially perpendicular to the inner walls of first inner fluid flow channel 310', wherein the internal diameter of the neck N is between d1 and d2, wherein secondary female section 306' has an internal diameter of d2 at top distal part 308 of primary Luer male connector 302', wherein d1 is smaller than d2, Vice versa, on the mating connector, primary Luer female connector 304', which is primarily female in shape, at its deepest point 312', the tapered cone 314' inverts back into a secondary male section 316', which returns back into the void space of primary Luer female connector 304'. The second inner fluid flow channel 318' extending along secondary male section 316' has a diameter of d1. Secondary male section 316' has a cone shape only at a tip 330 thereof (the part that is most remote from deepest point 312' of Luer female connector 304'. Cone shape tip 330 has two (but can be one or more) side slits 340 and 342 to permit allowance for tolerance. A top view of tip 330 is shown in the circle.

The diameter at the open end of primary Luer female connector (taper 6%) 304' is defined as "D".

The (external) diameter at the tip of the primary Luer male connector (taper 6%) 302' defined as "d".

In this manner, the two connectors (primary Luer male connector 302' and primary Luer female connector 304') still mate well, retain the dimensions "d" and "D" required by the standard but become more compact, and end with small diameters (d1) far less than "d" and "D", so that when gases flow from one to the other, minor changes in diameter are incurred and consequently reducing the effect on the rise time. In this manner inadvertent insertion of a larger sized male Luer into a smaller sized female Luer is prevented as required by the new standard.

It is noted that for simplicity, the original part of the male and female Luer are called the primary male and female sections, while the inverted sections are referred to as the secondary male and female sections.

According to some preferred embodiments, tip 330 of secondary male section 316' and secondary female section 306' have tapered angles whose tolerances are on the lower side of the tapered angle of the primary male and female sections (such as primary Luer male connector 302' and primary Luer female connector 304'). This is in order that the two fittings do not close first on the shorter and smaller secondary male and female sections, but mate primarily with the primary male and female cones. This effect is also assisted by the incomplete shape of tip 330 (slits) as discussed above.

According to some embodiments, an outer section of Luer connector 300' further includes screwing capability of one connector to its mating connector. Specifically, Luer male connector 302' includes threads 320' on an outer part thereof and primary Luer female connector 302' includes threads 322' on an outer part thereof.

According to some embodiments, when primary Luer male connector 302' and primary Luer female 304' mate with each other, secondary male section 316' is at least partially inserted to secondary female section 306'.

According to some embodiments, secondary male section 316' has a length L, which is higher than E max, wherein E max is the maximal distance between top distal part 308' of primary Luer male connector 302' and deepest point 312' of primary Luer female connector 304', when primary Luer male connector 302' and primary Luer female connector 304' are mated and wherein the tolerances of their cones are at their limits (see for example FIG. 1C) and hence mating occurs early in the mating process.

The second feature, according to some embodiments, is used for detecting that the parts as designed above only actuate the monitor when minimal leaks and negligible changes in diameter have been realized. For this purpose, several methods can be used, for example, a method which is based on detecting changes to an electric circuit by either closing the circuit, changing its inductance or capacitance or the resistance in part of it, etc. Alternatively, a method which is based on detecting optical or magnetic changes can also be applied. For example, if on the monitor side, a primary female Luer lock is used, two electrodes strip (for example 324' and 328') can line either the primary female opening (not shown) or tip 330 of secondary male section 316' (to a point where when mating primary Luer female connector 302' is correctly placed it should reach this point of electrodes strips 324' and 328'. On the mating primary Luer male connector 302', on the end thereof or internally at the end of secondary female section 306', a conducting ring 326' is placed. According to some embodiments, conducting ring 326' is positioned on all the inner circumference of secondary female section 306'. When the connectors are correctly and sufficiently in place, conducting ring 326' will close a circuit ending with electrode strips 324' and 328'. Electrode strips 324' and 328' are in turn connected to a circuit that can detect if there is conductance between the two or not, where on detection a signal is produced which consequently actuates the pump used to provide the sampling.

According to some embodiments, the term correctly placed defines a mating where there is no significant deterioration or slowing of rise time, and where negligible leaking of sampled gas can occur.

Inductance or capacitance can also be used, or any other method which can change electronic characteristics of a circuit when two dielectric or conducting materials and surfaces are positioned one relevant to the other. The overlap of the two material surfaces may result from the correct mating of the connectors, or from reaching a distance between them which will change the electric characteristics proportionally to the level of mating between the two connectors. These changes can be detected by the monitor, actuating the monitor sampling system only when correct mating is achieved.

In a further embodiment, the conducting ring could vary in resistance, which when measured, can be used as an indicator for a given type or class monitor or type and class patient interface as ended with the relevant connector.

Figure 3C:
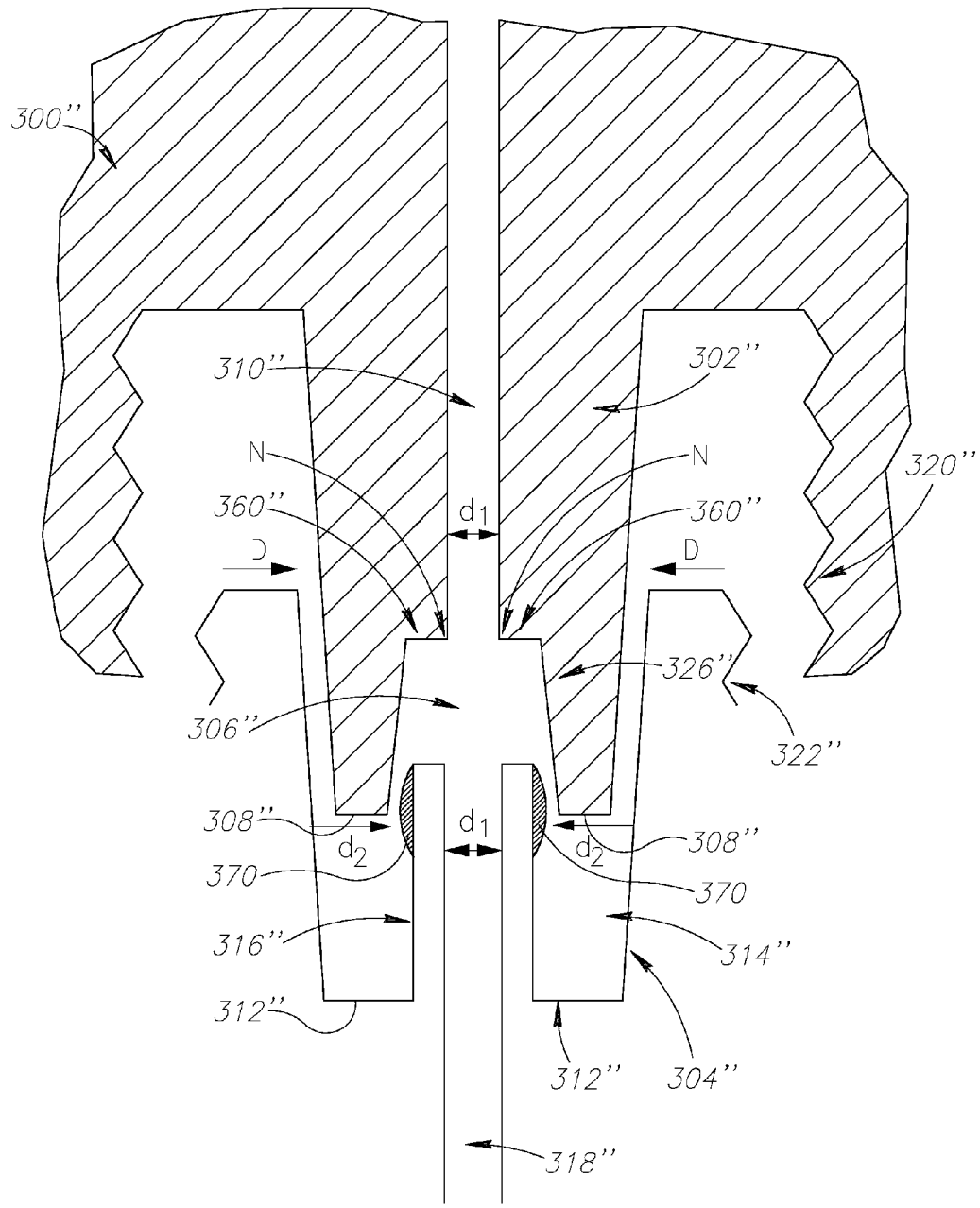

Another example of such inversion can be found in FIG. 3C, which shows a cross section of a Luer connector, according to embodiments of the invention. Luer connector 300" resembles Luer connector 300 of FIG. 3A excluding the structure of the secondary male section. Luer connector 300" includes primary Luer male connector 302" and primary Luer female connector 304". Primary Luer male connector 302" includes female part which forms secondary female section 306" having a cone shape and extending from the top distal part 308" of primary Luer male connector 302' back into primary Luer male connector 302" towards the proximal part thereof. The primary Luer male connector 302" includes a (centralized) first inner fluid flow channel 310" extending along its length from a proximal end of primary Luer male connector 302" to (and in fluid flow connection with) secondary female section 306". First inner channel 310" has a diameter of d1. At a connection point between first inner fluid flow channel 310" and the secondary female section 306" the internal diameter is increased to form a neck N having surface 360" essentially perpendicular to the inner walls of first inner fluid flow channel 310", wherein the internal diameter of the neck N is between d1 and d2, wherein secondary female section 306" has an internal diameter of d2 at top distal part 308" of primary Luer male connector 302", wherein d1 is smaller than d2, Vice versa, on the mating connector, primary Luer female connector 304", which is primarily female in shape, at its deepest point 312", the tapered cone 314" inverts back into a secondary male section 316", which returns back into the void space of primary Luer female connector 304". The second inner fluid flow channel 318' extending along secondary male section 316" has a diameter of d1. Secondary male section 316" has a sealing tip 370 at the part that is most remote from deepest point 312' of Luer female connector 304'. Sealing tip 370 is made of a material softer than that of secondary male section 316" (it may be made of, for example, an O ring, a PVC ball or any other material which can be used for sealing). The inner walls of secondary male section 316" may (as shown) or may not be tapered (cone shape).

The diameter at the open end of primary Luer female connector (taper 6%) 304" is defined as "D".

The (external) diameter at the tip of the primary Luer male connector (taper 6%) 302" defined as "d".

In this manner, the two connectors (primary Luer male connector 302" and primary Luer female connector 304") still mate well, retain the dimensions "d" and "D" required by the standard but become more compact, and end with small diameters (d1) far less than "d" and "D", so that when gases flow from one to the other, minor changes in diameter are incurred and consequently reduce the effect on the rise time. In this manner inadvertent insertion of a larger sized male Luer into a smaller sized female Luer is prevented as required by the new standard.

It is noted that for simplicity, the original part of the male and female Luer are called the primary male and female sections, while the inverted sections are referred to as the secondary male and female sections.

According to some embodiments, an outer section of Luer connector 300" further includes screwing capability of one connector to its mating connector. Specifically, Luer male connector 302" includes threads 320" on an outer part thereof and primary Luer female connector 302" includes threads 322" on an outer part thereof.

According to some embodiments, when primary Luer male connector 302" and primary Luer female 304" mate with each other, secondary male section 316" is at least partially inserted to secondary female section 306".

According to some embodiments, secondary male section 316" has a length L, which is higher than E max, wherein E max is the maximal distance between top distal part 308" of primary Luer male connector 302" and deepest point 312" of primary Luer female connector 304", when primary Luer male connector 302" and primary Luer female connector 304" are mated and wherein the tolerances of their cones are at their limits (see for example FIG. 1C) and hence mating occurs early in the mating process.

According to some embodiments (not shown), similar to those described in FIG. 3A, a second feature, according to some embodiment, may be used for detecting that the parts as designed above only actuate the monitor when minimal leaks and negligible changes in diameter have been realized.

Figure 4:
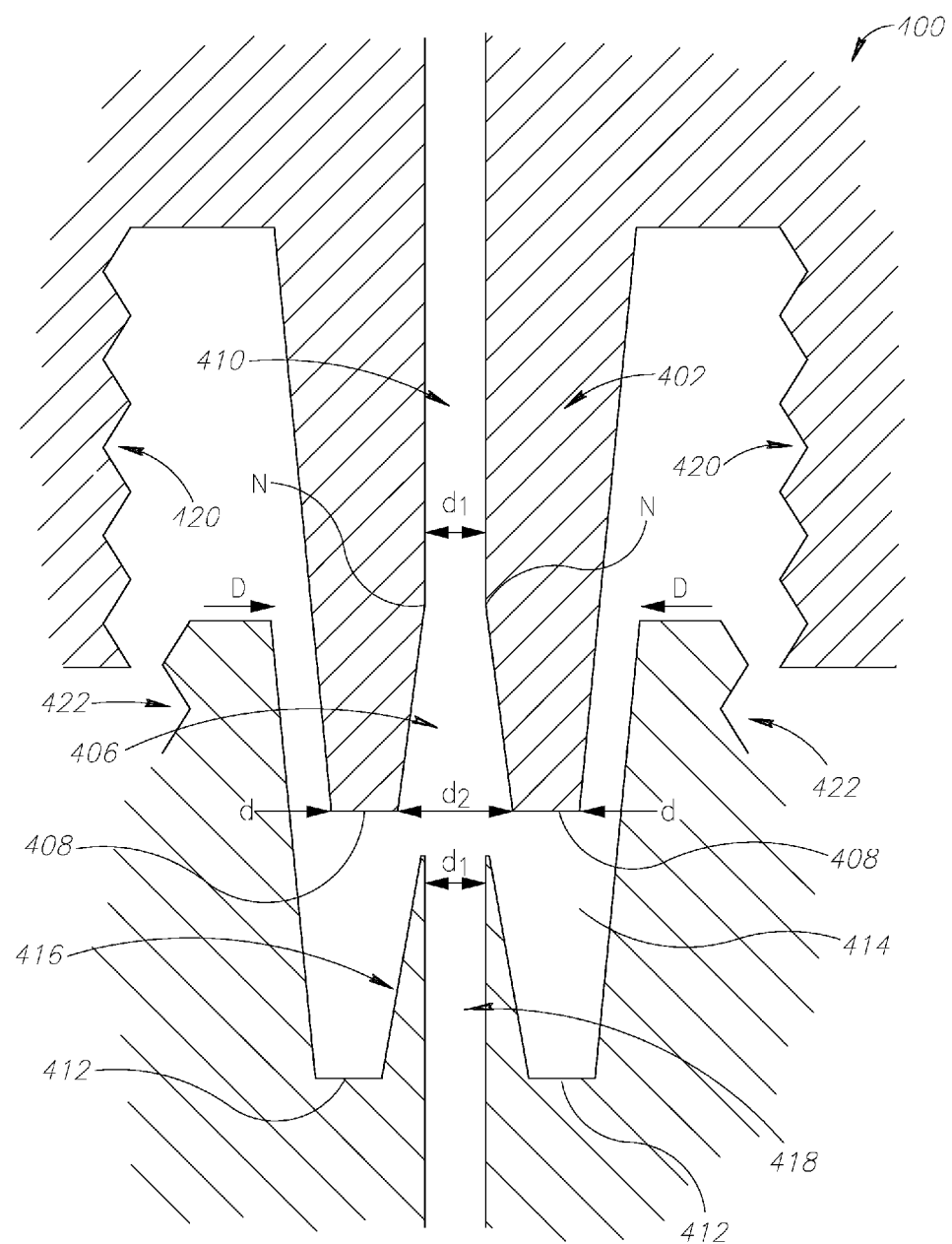
FIG. 4 shows a cross section of a Luer connector, according to embodiments of the invention.

Another example of such inversion can be found in FIG. 4, which shows a cross section of a Luer connector, according to embodiments of the invention. Luer connector 400 includes primary Luer male connector 402 and primary Luer female connector 404. Primary Luer male connector 402 includes female section which forms secondary female section 406 having a cone shape and extending from the top distal part 408 of primary Luer male connector 402 back into primary Luer male connector 402 towards the proximal part thereof. The primary Luer male connector 402 includes a (centralized) first inner fluid flow channel 410 extending along its length from a proximal end of primary Luer male connector 402 to (and in fluid flow connection with) secondary female section 406. First inner channel 410 has a diameter of d1. Secondary female section 406 is tapered such that it starts having a diameter of d1 and tapers to an internal diameter of d2 at top distal part 408 of primary Luer male connector 402, such that d1 is smaller than d2.

Comparably, on the mating connector, primary Luer female connector 404, which is primarily female in shape, at its deepest point 412, the tapered cone 414 inverts back into a secondary male section 416, which has a cone shape and returns back into the void space of primary Luer female connector 404. The second inner fluid flow channel 418 extending along secondary male section 416 has a diameter of d1.

The diameter at the open end of primary Luer female connector (taper 6%) 404 is defined as "D".

The (external) diameter at the tip of the primary Luer male connector (taper 6%) 402 defined as "d".

In this manner, the two connectors (primary Luer male connector 402 and primary Luer female connector 404) still mate well, retain the dimensions "d" and "D" required by the standard but become more compact, and end with small diameters (d1) far less than "d" and "D", so that when gases flow from one to the other, minor changes in diameter are incurred and consequently reduce the effect on the rise time. In this manner inadvertent insertion of a larger sized male Luer into a smaller sized female Luer is prevented as required by the new standard.

It is noted that for simplicity, the original part of the male and female Luer are called the primary male and female sections, while the inverted sections are referred to as the secondary male and female sections.

According to some preferred embodiments, the secondary male and female sections (such as secondary male section 416 and secondary female section 406) have tapered angles whose tolerances are on the lower side of the tapered angle of the primary male and female sections (such as primary Luer male connector 402 and primary Luer female connector 404). This is in order that the two fittings do not close first on the shorter and smaller secondary male and female sections, but mate primarily with the primary male and female cones. It is also possible to produce the secondary male Luer section from a softer material than that used to make the secondary female section, where in this manner the secondary male section can be made of the same taper and its tolerances as the primary Luer.

According to some embodiments, an outer section of Luer connector 400 further includes screwing capability of one connector to its mating connector. Specifically, Luer male connector 402 includes threads 420 on an outer part thereof and primary Luer female connector 404 includes threads 422 on an outer part thereof.

According to some embodiments (not shown), similar to those described in FIG. 3A, a second feature, according to some embodiment, may be used for detecting that the parts as designed above only actuate the monitor when minimal leaks and negligible changes in diameter have been realized.

Luer Connector—Second Aspect:

According to some embodiments, this aspect includes at least one, though preferably two major features. Primarily a mechanical design that on one hand complies with the new standard ISO/CD 80369-2, but dictates that when the fittings are mated, the changes and discontinuities in diameter of the conduits within which the breath samples flow are reduced to a minimum, and this for a minimum length. This design further dictates minimal leak, even when both the male and female connectors are mated weakly. Secondly, the design provides a simple means for detecting when minimal leak as well as minimal effect on rise time has been achieved and only then an automatic detection system activates the monitor sampling capability.

This design also benefits from a further advantage yet mentioned: A design that can solve a further problem that will be caused by adhering to the new standard. As mentioned, the new standard dictates a larger dimensioned connector for mating between male and female parts. Thus not only will connectors joined to patient interfaces, consumables and loose parts be required to change but so will their counterparts on devices (such as capnographs). The relevant devices, already in the field, on the market etc. and designed with existing Luer connectors have predefined layouts and space allocations on the devices panel as well as space requirements within the device. The new connectors will dictate more space, both in radius and in depth. Since the devices when designed did not take these new dimensions into account, it is possible that pre-existing devices may require large changes to accommodate the new Luer connectors.

Hence with this aspect, according to some embodiments of the invention, the outer section of the Luer connector typically used to date for providing a screwing capability of one connector to its mating connector (see FIG. 4, threads 420 on the outer part of Luer male connector 402 and threads 422 on the outer part of primary Luer female connector 404) is removed, and this screwing capability and structure is transferred to the central axis (see FIG. 5 herein below).

According to some embodiments, this first feature with this aspect is accomplished by using a means comparable to optical systems where mechanical dimensions of an imaging system with long focal lengths dictate long optical paths. In such systems the optical paths are either folded upon themselves or redirected by minors in order to reduce the lengths of the total system. In a similar way, this folding principal is used with male and female Luer locks. As discussed above, for optimal design with a Capnograph, the 6% tapered conical fitting would have preferably been increased in length so as to reach the point where the cone intersects the internal orifice of the internal conduit used for transmitting the breath sample. If this were the case, when the male and female Luer would have mated, theoretically there would have been only a negligible change in diameter when moving from the male to female connector and hence incurring negligible effect on the sampled breath rise time.

Such a design, even if it would have been acceptable with its extremely long connector, is unacceptable by definition in the said new standard, where the final (external) diameter at the end of the tapered connector is clearly limited to a diameter of 4.58 mm on the male side (defined by the letter "d") and 4.87 mm on the female side (defined by the letter "D") (see Table 1). To overcome this, while still complying with the above values for "d" and "D", it is possible to fold over the tapered cone, so that the male connector is extended in length by inverting the male extension into a female section which returns back into the male extension. The inversion is made when the (external) diameter of the male extension reaches the diameter "d", the nominal diameter as defined by the standard. This male (hollow) extension does not continue with a 6% tapered conical shaped hollow cone, but has constant internal diameter and includes an appropriate thread structure matching a similar thread structure to be placed on the mating connector.

Figure 5:
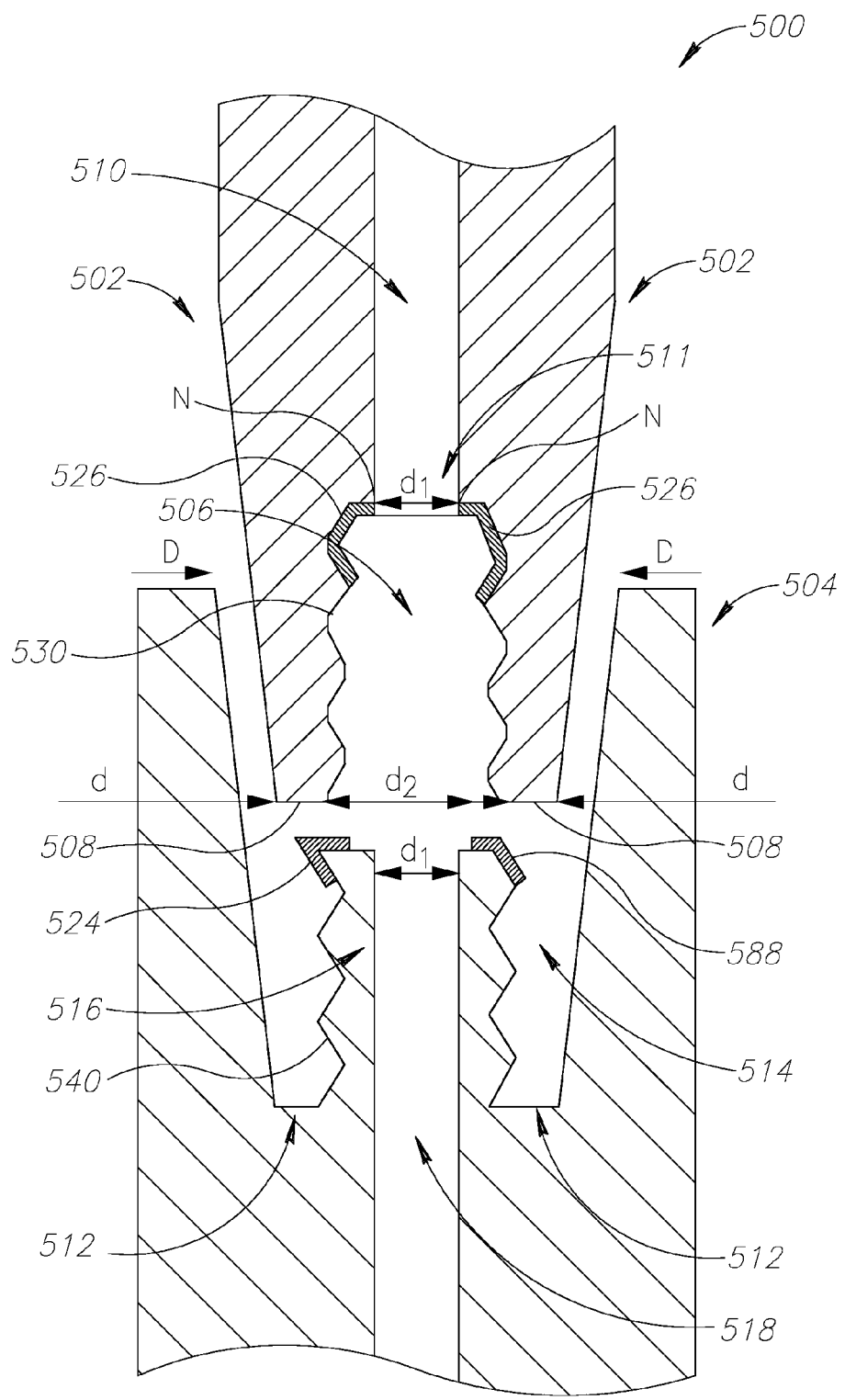
FIG. 5 shows a cross section of a Luer connector, according to embodiments of the invention.

Comparably, on the mating connector which is primarily female in shape, at its deepest point, the tapered cone inverts back into a constant diameter extension which includes an appropriate thread structure matching the similar thread structure placed on the mating connector (see FIG. 5).

For simplicity, the original part of the male and female Luer will be called the primary male and female sections, while the inverted sections are referred to as the secondary male thread and female thread sections.

Hence, the two connectors are screwed firmly together in order to mate the two opposing 6% tapered cones using the smaller diameter threaded secondary sections.

In this manner, the two connectors still mate well, retain the dimensions "d" and "D", but become more compact, and end with small diameters far less than "d" and "D", so that when gases flow from one to the other, minor changes in diameter are incurred consequently reducing the effect on the rise time. In this manner, inadvertent insertion of a larger sized male Luer into a smaller sized female Luer is prevented as required by the new standard. Further, the entire connector dimensions are reduced sufficiently that despite the use of larger tapered Luers, the overall size is reduced by removing the external thread section, consequently permitting a one to one fitting with existing designed device panels.

An example of a Luer connector according to the Second Aspect can be found in FIG. 5, which shows a cross section of a Luer connector, according to embodiments of the invention. Luer connector 500 includes primary Luer male connector 502 and primary Luer female connector 504. Primary Luer male connector 502 includes female section which forms secondary female section 506 having threads 530 and extending from the top distal part 508 of primary Luer male connector 502 back into primary Luer male connector 502 towards the proximal part thereof. The primary Luer male connector 502 includes a (centralized) first inner fluid flow channel 510 extending along its length from a proximal end of primary Luer male connector 502 to (and in fluid flow connection with) secondary female section 506. First inner channel 510 has a diameter of d1. Secondary female section 506 has a diameter of d1 at a proximal end 511 thereof (where it connects with to first inner channel 510) and an internal diameter of d2 at top distal part 508 of primary Luer male connector 502, such that d1 is smaller than d2.

Comparably, on the mating connector, primary Luer female connector 504, which is primarily female in shape, at its deepest point 512, the tapered cone 514 inverts back into a secondary male section 516, which has threads 540 and returns back into the void space of primary Luer female connector 504. The second inner fluid flow channel 518 extending along secondary male section 516 has a diameter of d1. Threads 530 of secondary female section 506 and threads 540 of secondary male section 516 are configured to mate. As noted herein above the Luer connectors, according to embodiment of the invention, can either be of normal Luer or of slip Luer, i.e. with external thread or without external thread, respectively. However, with Luer connectors such as Luer connector 500 there is no need an external thread, which may be an advantage.

The diameter at the open end of primary Luer female connector (taper 6%) 504 is defined as "D".

The diameter at the tip of the primary Luer male connector (taper 6%) 502 defined as "d".

In this manner, the two connectors (primary Luer male connector 502 and primary Luer female connector 504) still mate well, retain the dimensions "d" and "D" required by the standard but become more compact, and end with small diameters (d1) far less than "d" and "D", so that when gases flow from one to the other, minor changes in diameter are incurred consequently reducing the effect on the rise time. In this manner, inadvertent insertion of a larger sized male Luer into a smaller sized female Luer is prevented as required by the new standard.

It is noted that for simplicity, the original part of the male and female Luer are called the primary male and female sections, while the inverted sections are referred to as the secondary male and female sections.

The second feature, according to some embodiment, is used for detecting that the parts as designed above only actuate the monitor when minimal leaks and negligible changes in diameter have been realized. For this purpose, several methods can be used, for example, a method which is based on detecting changes to an electric circuit by either closing the circuit, changing its inductance or capacitance or the resistance in part of it, etc. Alternatively, a method which is based on detecting optical or magnetic changes can also be applied. For example, if on the monitor side, a primary female Luer lock is used, (two) electrodes strip (for example 524 and 528) can line either the primary female opening (not shown) or secondary male section 516 (to a point where when mating primary Luer male connector 502 is correctly placed it should reach this point of electrodes strips 524 and 528. On the mating primary Luer male connector 502, on the end thereof or internally at the end of secondary female section 506, a conducting ring 526 is placed. According to some embodiments, conducting ring 526 is positioned on the inner circumference of secondary female section 506. When the connectors are correctly and sufficiently in place, conducting ring 526 will close a circuit ending with electrode strips 524 and 528. Electrode strips 524 and 528 are in turn connected to a circuit that can detect if there is conductance between the two or not, where on detection a signal is produced which consequently actuates the pump used to provide the sampling.

According to some embodiments, the term correctly placed defines a mating where there is no significant deterioration or slowing of rise time, and where negligible leaking of sampled gas can occur.

Inductance or capacitance can also be used, or any other method which can change electronic characteristics of a circuit when two dielectric or conducting materials and surfaces are positioned one relevant to the other, where the overlap of two material surfaces result from the correct mating of the connectors, or where a distance between them will change the electric characteristics that are proportional to the level of mating between the two connectors. These changes can be detected by the monitor, actuating the monitor sampling system only when correct mating is achieved.

In a further embodiment, the conducting ring could vary in resistance, when measured, can be used as an indicator for a given type or class monitor or type and class patient interface as ended with the relevant connector.

Luer Connector—Third Aspect:

According to some embodiments, this aspect includes at least one, though preferably two major features, Primarily a mechanical design that on one hand complies with the new standard ISO/CD 80369-1.2, but dictates that when the fittings are mated, the changes and jumps in diameter of the conduits within which the breath samples flow are reduced to a minimum, and this for a minimum length. This design further dictates minimal leak, even when both the male and female connectors are mated weakly. Secondly, the design provides a simple means for detecting when minimal leak as well as minimal effect on rise time has been achieved and only then a an automatic detection system activates the monitor sampling capability.

According to some embodiments, the first feature is accomplished by using a means comparable to optical systems where mechanical dimensions of an imaging system with long focal lengths dictate long optical paths. In such systems the optical paths are either folded upon themselves or redirected by mirrors in order to reduce the lengths of the total system. In a similar way, this folding principal is used with male and female Luer locks. As discussed above, for optimal design with a Capnograph, the 6% tapered conical fitting would have preferably been increased in length so as to reach the point where the cone intersects the internal orifice of the internal conduit used for transmitting the breath sample. If this were the case, when the male and female Luer would have mated, theoretically there would have been only a negligible change in diameter when moving from the male to female connector and hence incurring negligible effect on the sampled breath rise time.

Such a design, even if it would have been acceptable with its extremely long connector, is unacceptable by definition in the said new standard, where the final diameter at the end of the tapered connector is clearly limited to a diameter of 4.58 mm on the male side (defined by the letter "d") and 4.87 mm on the female side (defined by the letter "D") (see Table 1). To overcome this, while still complying with the above values for "d" and "D", it is possible to fold over the tapered cone, so that the male connector is extended in length by inverting the male extension into a female section which returns back into the male extension. The inversion is made when the diameter of the male extension reaches the diameter "d", the nominal diameter as defined by the standard. This female type extension can be either conical or straight in shape whose depth is limited with respect to the end of the primary male section. It ends internally with a female abutting section (see for example, FIG. 6 herein below).

On the other hand, on the mating connector which is primarily female in shape, at its deepest point, and along its central axis, a separate, spring loaded tubular insert inverts back into the void space of the female section (see for example, FIG. 6 herein below). The spring loaded tubular sections have a diameter and shape that fits the female extension of its opposing connector. When the two connectors are mated, the extension of the spring loaded tube is so designed as to abut with the abutting section of the opposing connector at an early stage of the mating process, where any further pushing or screwing of the two connectors together will create force on the spring, pushing the spring loaded tubular extension backwards, through at the same time retaining the tube abutted to the female abutting section.

For simplicity, the original part of the male and female Luer will be called the primary male and female sections, while the inverted sections are referred to as the spring loaded tubular section and the secondary female sections.

In this manner, the two connectors will mate well, retaining the dimensions "d" and "D", but become more compact, and end with negligible diameters far less than "d" and "D", so that when gases flow from one to the other, minor changes in diameter if at all are incurred consequently reducing the effect on the rise time. In this manner, inadvertent insertion of a larger sized male Luer into a smaller sized female Luer is prevented as required by the new standard.

According to some embodiments, the spring loaded section can be shaped as tubular or conical. Further, according to some embodiments, the abutting regions may be rounded for better matching. According to some embodiments, the depth of the protruding spring loaded tubing, should take into consideration the tolerances of 6% tapered cone Luers in order to accommodate for the possible final positions when mated.

Figure 6:
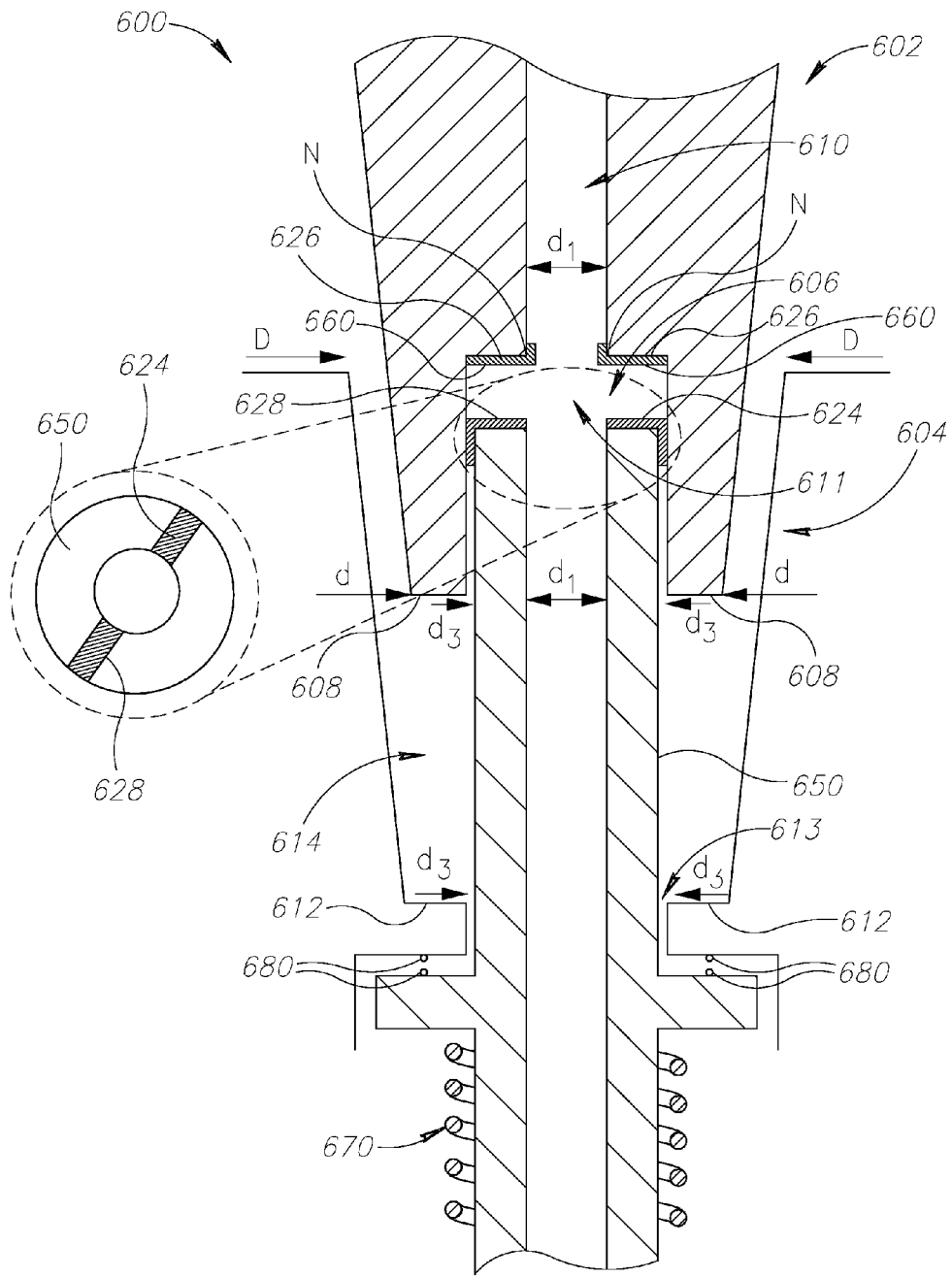
FIG. 6 shows a cross section of a Luer connector, according to embodiments of the invention.

An Example of a Luer connector according to the Third Aspect can be found in FIG. 6, which shows a cross section of a Luer connector, according to embodiments of the invention. Luer connector 600 includes primary Luer male connector 602 and primary Luer female connector 604. Primary Luer male connector 602 includes female section which forms secondary female section 606 extending from the top distal part 608 of primary Luer male connector 602 back into primary Luer male connector 602 towards the proximal part thereof. Primary Luer male connector 602 includes a (centralized) first inner fluid flow channel 610 extending along its length from a proximal end of primary Luer male connector 602 to (and in fluid flow connection with) secondary female section 606. First inner channel 610 has a diameter of d1. Secondary female section 606 has a diameter of d1 at a proximal end 611 thereof (where it connects with to first inner channel 610) and a diameter of d3 at top distal part 608 of primary Luer male connector 602, such that d1 is smaller than d3.

Comparably, on the mating connector, primary Luer female connector 604, which is primarily female in shape, at its deepest point 612, the tapered cone 614 has an opening 613 having a diameter of d3. Through opening 613 and along a central axis of primary Luer female connector 604, a separate, spring loaded tubular insert 650 inverts back into the void space of tapered cone 614 of primary Luer female connector 604. Spring loaded tubular (section) insert 650 has a diameter and shape that fits secondary female section 606 of primary Luer male connector 602. It is noted that the spring loaded insert may be tubular as shown (spring loaded tubular insert 650) but may also have other shapes or forms. For example it could be conical or partially conical and configure to connect with a matching conical or partially conical secondary female section. When the two connectors (primary Luer male connector 602 and primary Luer female connector 604) are mated, spring loaded tubular insert 650 is designed such that its top distal section is inserted into secondary female section 606 of the opposing connector (primary Luer male connector 602) at an early stage of the mating process, where any further pushing or screwing of the two connectors together will create force on spring 670, pushing spring loaded tubular insert 650 backwards. Though at the same time, retaining spring loaded tubular insert 650 abutted to the female abutting section 660. The inner diameter of spring loaded tubular insert 650 is d1, same as the diameter of first inner channel 610 of primary Luer male connector 602, such that when spring loaded tubular insert 650 is designed to abut with abutting section 660 of primary Luer male connector 602 a continuous inner channel having a diameter of d1 is formed.

It is noted that, according to some embodiments, the spring loaded tubular insert may also be conical and configured to fit a conical secondary female section when mated.

The diameter at the open end of primary Luer female connector (taper 6%) 604 is defined as "D".

The diameter at the tip of the primary Luer male connector (taper 6%) 602 defined as "d".

In this manner, the two connectors (primary Luer male connector 602 and primary Luer female connector 604) still mate well, retain the dimensions "d" and "D" required by the standard but become more compact, and end with small diameters (d1) far less than "d" and "D", so that when gases flow from one to the other, minor changes in diameter are incurred consequently reducing the effect on the rise time. In this manner, inadvertent insertion of a larger sized male Luer into a smaller sized female Luer is prevented as required by the new standard.

The second feature, according to some embodiment, is used for detecting that the parts as designed above only actuate the monitor when minimal leaks and negligible changes in diameter have been realized. For this purpose, several methods can be used, for example, a method which is based on detecting changes to an electric circuit by either closing the circuit, changing its inductance or capacitance or the resistance in part of it, etc. Alternatively, a method which is based on detecting optical or magnetic changes can also be applied. For example, if on the monitor side, a primary female Luer lock is used, (two) electrodes strip (for example 624 and 628) can line either the primary female opening (not shown) or on the tip of spring loaded tubular insert 650 (to a point where when mating primary Luer male connector 602 is correctly placed it should reach this point of electrodes strips 624 and 628. On the mating primary Luer male connector 602, on the end thereof or internally at the end of secondary female section 606, a conducting ring 626 is placed (on abutting section 660). When the connectors are correctly and sufficiently in place, conducting ring 626 will close a circuit ending with electrode strips 624 and 328. Electrode strips 324 and 328 are in turn connected to a circuit that can detect if there is conductance between the two or not, where on detection a signal is produced which consequently actuates the pump used to provide the sampling.

According to some embodiments, the term correctly placed defines a mating where there is no significant deterioration or slowing of rise time, and where negligible leaking of sampled gas can occur.

According to some embodiments, electrodes 680 may be used on either side of the moving spring loaded tubular insert 650. Electrodes 680 are configured to be connected before any mating connector enters, and to be separated, to break the circuit when the spring loaded parted is pushed inwards as would happen when a correct mating has been connected.

Inductance or capacitance can also be used, or any other method which can change electronic characteristics of a circuit when two dielectric or conducting materials and surfaces are positioned one relevant to the other, where the overlap of two material surfaces result from the correct mating of the connectors, or where a distance between them will change the electric characteristics that is proportional to the level of mating between the two connectors. These changes can be detected by the monitor, actuating the monitor sampling system only when correct mating is achieved.

In a further embodiment, the conducting ring could vary in resistance, when measured, can be used as an indicator for a given type or class monitor or type and class patient interface as ended with the relevant connector.

Figure 7:
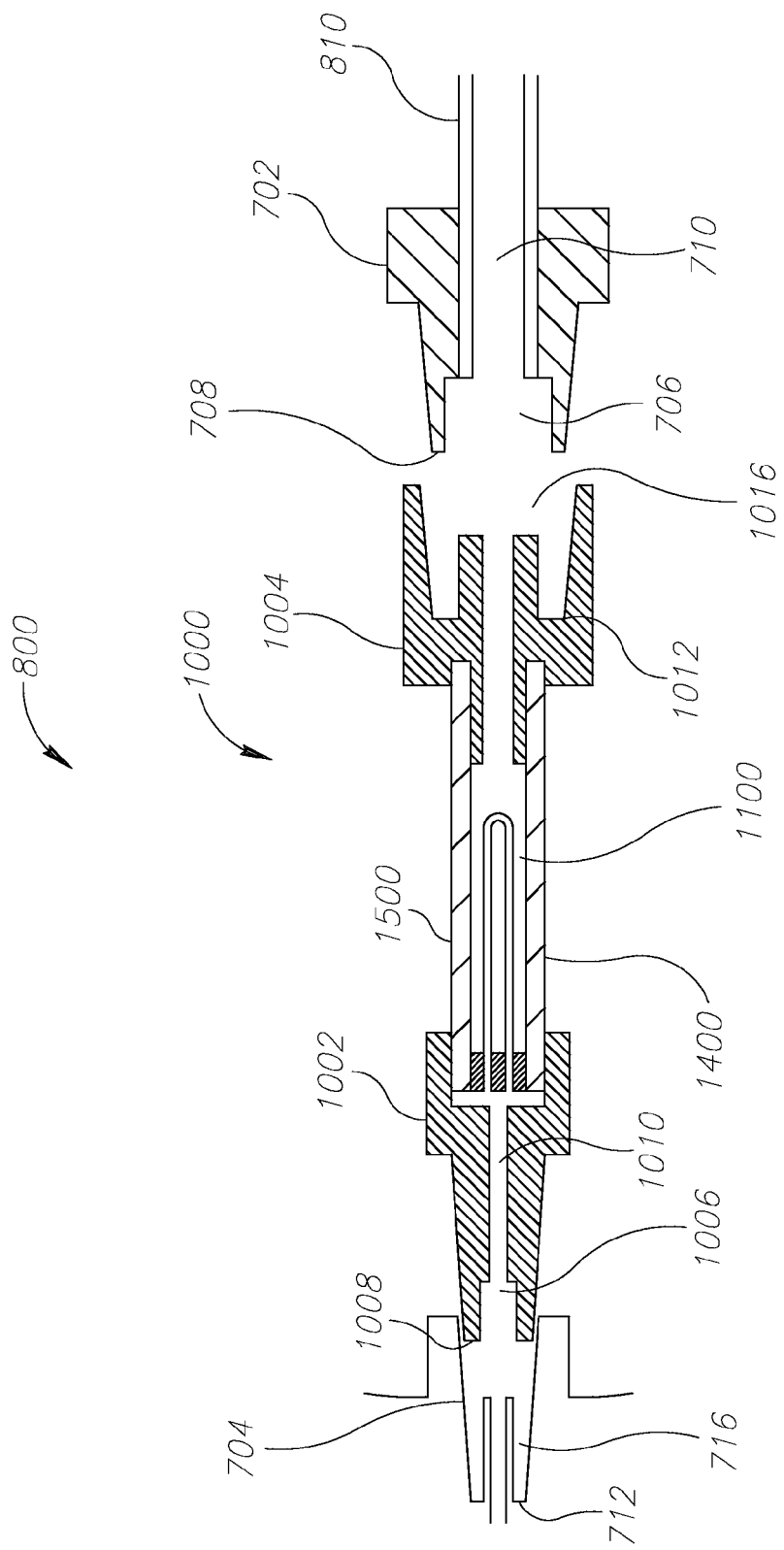
FIG. 7 shows a cross section of a filter comprising Luer connectors for assembly into a sampling line, according to embodiments of the invention.

Luer Connector—Fourth Aspect:

According to some embodiments, this aspect includes at least one, though preferably three major features. Primarily a mechanical design that on one hand complies with the new standard ISO/CD 80369-2, but dictates that when the fittings are mated, the changes and discontinuities in diameter of the conduits within which the breath samples flow are reduced to a minimum, and this for a minimum length. This design further dictates minimal leak, even when both the male and female connectors are mated weakly. Secondly, the design provides a simple means for detecting when minimal leak as well as minimal effect on rise time has been achieved and only then an automatic detection system activates the monitor sampling capability. Thirdly, the design enables coupling an appropriate filtering system designed to absorb liquids and hindering them from reaching sensitive monitors such as e.g., a capnograph, by using Luer connectors as those essentially described above. Hence, the design enables modulating the sampling line by for example exchanging a patient cannula while maintaining the filter without jeopardizing safety. This since only when an appropriate filter is connected to the appropriate connectors on the patient cannula and on the monitor, the automatic detection system activates the monitor sampling capability An Example of a modulatory sampling line according to the Fourth Aspect of the invention can be found in FIG. 7.

According to some embodiments of the invention, disclosed is a sampling line comprising a sampling tube encompassing a filter housing, wherein said filter housing comprises a primary Luer male connector adapted to connect to the primary Luer female connector of a monitor.

According to some embodiments of the invention, disclosed is a modulatory sampling line 800, comprising a filter housing 1000, connecting between a primary Luer male connector 702 of a patient sampling tube 810, and a primary Luer female connector 704 which is a part of a monitor such as for example a capnograph. According to some embodiments of the invention, the connections are made by using sequential Luer connectors.

Filter housing 1000 comprises a primary Luer female connector 1004 on one end thereof (for example on the patient side) and a primary Luer male connector 1002 on the other end thereof (for example on the monitor side), a filter 1100 adapted to absorb liquids and at least one conducting strip, such as conducting strips 1400 and 1500.

According to some embodiments, filter 1100 can be any filter adapted to absorb liquids such as, but not limited to, a hollow fiber filter.

According to some embodiments filter housing 1000 further comprises a blocking agent 1200 adapted to prevent exhaled air from circumventing filter 1000. Alternatively, filter 1100 can be molded on filter housing 1000 so as to prevent exhaled air from circumventing said filter.

According to some embodiments, primary Luer male connector 1002 includes a female part which forms a secondary female section 1006 extending from a top distal part 1008 of primary Luer male connector 1002 back into primary Luer male connector 1002 towards the proximal part thereof. Primary Luer male connector 1002 includes a (centralized) first inner fluid flow channel 1010 extending along its length from a proximal end of primary Luer male connector 1002 to (and in fluid flow connection with) secondary female section 1006 as essentially described above.

According to some embodiments, primary Luer male connectors 702 includes female part which forms a secondary female section 706 extending from a top distal part 708 of primary Luer male connector 702 back into primary Luer male connector 702 towards the proximal part thereof. Primary Luer male connector 702 includes a (centralized) first inner fluid flow channel 710 extending along its length from a proximal end of primary Luer male connector 702 to (and in fluid flow connection with) secondary female section 706 as essentially described above.

Primary Luer female connector 1004, which is primarily female in shape, at its deepest point 1012, inverts back into a secondary male section 1016, which returns back into the void space of primary Luer female connector 1004, wherein said secondary male section 1016 comprises a second inner fluid flow channel 1018 extending along the length thereof as essentially described above.

Primary Luer female connector 704, which is primarily female in shape, at its deepest point 712, inverts back into a secondary male section 716, which returns back into the void space of primary Luer female connector 704 as essentially described above.

According to some embodiments, primary Luer female connector 1004 is adapted to be connected to primary Luer male connector 702 of patient sampling tube 810, as essentially described above. According to some embodiments, primary Luer male connector 1002 is adapted to be connected to primary Luer female connector 704 of a monitor such as for example a capnograph, as essentially described above.

According to some embodiments, sampling line 800 is configured to allow activation of the monitoring device only when its components are correctly assembled and an electric circuit is closed. According to some embodiments, the monitor, such as a capnograph, is only actuated when the entire sampling line 800 is correctly assembled. Specifically, the monitor is only actuated when primary Luer female connector 1004 is correctly and/or sufficiently connected to primary Luer male connector 702 and when primary Luer male connector 1002 is correctly and/or sufficiently connected to primary Luer female connector 704. According to some embodiments connecting primary male Luer connector 1002 to primary Luer female connector 704 will not actuate the monitor. This is in order to avoid that the monitor will work without being connected to a patient, thereby causing a reduced lifespan of the monitor.

Figure 8A:
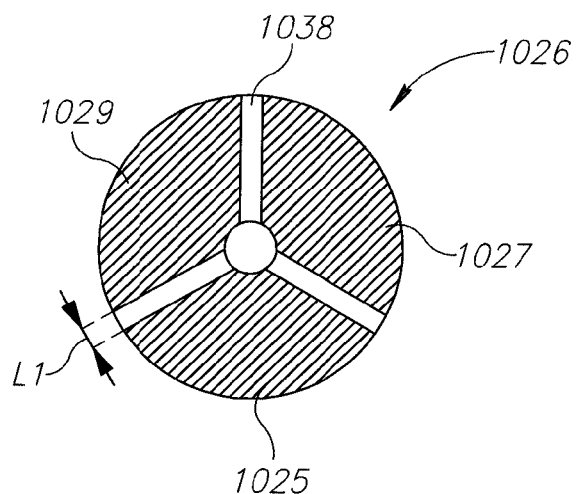
FIG. 8 schematically illustrate conducting elements according to embodiments of the invention.

According to some embodiments, secondary female section 1006 of primary Luer male connector 1002 comprises a first conducting element such as for example conducting element 1026 schematically illustrated in FIG. 8a, and secondary male section 1016 of primary Luer female connector 1004 comprises a second conducting element, such as for example conducting element 1026 schematically illustrated in FIG. 8a. According to some embodiments, the first and second conducting element each comprise at least three receiving conductor pads, such as conducting pads 1025, 1027, 1029 wherein each receiving conductor pad is separated from its neighboring conducting pad by a non-conducting gap such as gap 1030. According to some embodiments, first conducting element and second conducting element may be identical. According to some embodiments, first conducting element and second conducting element may be different.

Figure 8B:
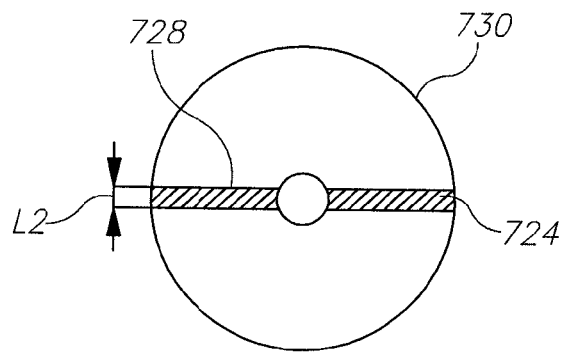

According to some embodiments, secondary male section 716 of the primary Luer female connector 704 of the monitor comprises a third conducting element, such as conducting strips 724 and 728 schematically illustrated in FIG. 8b. According to some embodiments conducting strips 724 and 728 are separated by a non-conducting gap 730.

According to some embodiments the width L1 of the gaps such as gap 1030 (FIG. 8a) is less than the width L2 of each of conducting strips 724 and 728 (FIG. 8b).

Figure 8C:
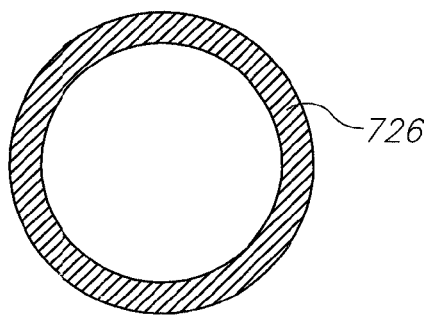

According to some embodiments, secondary female section 706 of primary Luer male connector 702 comprises a fourth conducting element such as conducting ring 726 schematically illustrated in FIG. 8c.

According to some embodiments, when only primary Luer male connector 1002 is correctly connected to primary Luer Female connector 704 of the monitor an electric circuit is not closed and the monitor is not actuated.

According to some embodiments, only when primary Luer male connector 1002 is correctly connected to primary Luer female connector 704 of the monitor, and when primary Luer female connector 1004 is correctly connected to primary Luer male connector 702 of sampling tube 810 an electric circuit is closed and the monitor is actuated.

According to some embodiments, the term correctly placed as referred to herein, defines a mating between a primary Luer female connector and a primary Luer male connector where there is no significant deterioration or slowing of rise time, and where negligible leaking of sampled gas can occur.

It is to be understood that, several methods can be used for the purpose of activating the monitor only upon proper assembly of the entire sampling line (such as sampling line 800). For example, a method which is based on detecting changes to an electric circuit by either closing the circuit, changing its inductance or capacitance or the resistance in a part of it, etc. According to some embodiments, conducting strips 1400 and 1500 are adapted to electrically connect between primary female Luer connector 1004 and primary male connector 1002.

According to some embodiments, conducting strips 1400 and 1500 are adapted to conduct between primary female Luer connector 1004 and primary male connector 1002.

Thus, according to some embodiments, once sampling line 800 is correctly assembled, an electric circuit is closed between: electrodes strips 724 and 728 on primary Luer female connector 704 of a monitor, first conducting element such as conducting element 1026 on primary male connector 1002, conducting strips 1400 and 1500, second conducting element such as conducting element 1026 on primary female Luer connector 1004 and conducting ring 726 on primary male connector 702 of patient sampling tube 810.

It is to be understood by the skilled in the art, that inductance or capacitance can also be used, or any other method which can change electronic characteristics of a circuit when two dielectric or conducting materials and surfaces are positioned one relevant to the other. According to some embodiments, the overlap of two material surfaces may result from the correct mating of the connectors, or from reaching a distance between them which will change the electric characteristics proportionally to the level of mating between the two connectors. These changes can be detected by the monitor, actuating the monitor sampling system only when correct mating is achieved.

In a further embodiment, the conducting rings could vary in resistance, which when measured, can be used as an indicator for a given type or class monitor or type and class patient interface as ended with the relevant connector.

It is to be understood by the skilled in the art that modulatory sampling line 800 facilitates to exchange some parts of modulatory sampling line 800, such as for example patient sampling tube 810, while facilitating reuse of other parts of modulatory sampling line 800 such as for example filter housing 1000.

It is noted that for simplicity, the original part of the male and female Luer are called the primary male and female sections, while the inverted sections are referred to as the secondary male and female sections.

Likewise, it is to be understood, that the primary Luer male connector and the primary Luer female connector may be used interchangeably, for example, the primary Luer male connector may be used at the monitor side and the primary Luer female connector may be used at the filter side, or vice versa, the primary Luer female connector may be used at the monitor side and the primary Luer male connector may be used at the filter side. Similarly, the primary Luer male connector may be used at the patient sampling tube side and the primary Luer female connector may be used at the filter side, or vice versa, the primary Luer female connector may be used at the patient sampling tube side and the primary Luer male connector may be used at the filter side.

According to some embodiments, the same primary Luer connectors may be used on the monitor side and on the sample tube side. For example a primary Luer female connector may be used on both the monitor side and on the sample tube side whereas a primary Luer male connector may be used on both sides of the filter. For example a primary Luer male connector may be used on both the monitor side and on the sample tube side whereas a primary Luer female connector may be used on both sides of the filter. This embodiment avoids connecting a sampling tube (not having a filter) directly to a monitor without encompassing a filter thereby potentially harming the monitor.

It is noted that the Luer connectors, according to embodiment of the invention, can either be of normal Luer or of slip Luer, i.e. with external thread or without external thread, respectively.

Furthermore, an ordinary skilled in the art will understand that all the Luer connectors used in this aspect of the invention can be any of the Luer connectors disclosed herein and described in FIGS. 3-6.

In addition to the exemplary aspects and embodiments described above, further aspects and embodiments will become apparent by reference to the figures and by study of the following detailed description.

I claim:

1. A Luer connector for use in a respiratory gas sampling and/or delivery tubing systems, the connector comprising:
   a primary Luer male connector, having a form of a tapered cone, comprising a secondary female section extending from a top distal part of said primary Luer male connector back towards a proximal part thereof, wherein said primary Luer male connector comprises a first inner fluid flow channel extending along its length from a proximal end thereof to and in fluid flow connection with said secondary female section, wherein said first inner fluid flow channel has a diameter of approximately d1, wherein the diameter increases at a connection point between said first inner fluid flow channel and said secondary female section to form a neck N, wherein the internal diameter of said neck N is between d1 and d2, wherein said secondary female section has an internal diameter of d2 at a top distal part of said primary Luer male connector, wherein d1 is smaller than d2,
   wherein when said primary Luer male connector mates with a primary Luer female connector having a secondary male section, said secondary male section is at least partially inserted into said secondary female section, thereby extending said inner fluid flow channel having diameter d1 throughout said primary Luer male connector and said primary Luer female connector, such that said diameter d1 is constant throughout said primary Luer male connector and said primary Luer female connector.

2. A Luer connector for use in a respiratory gas sampling and/or delivery tubing systems, the connector comprising:
   a primary Luer female connector having a form of a tapered cone, wherein at its deepest point, the tapered cone inverts back into a secondary male section and returns into a void of said primary Luer female connector, wherein said secondary male section comprises an outer wall and an inner wall, said inner wall being non-tapered thereby forming an inner fluid flow channel, of a diameter d1, extending along said secondary male section and along said primary Luer female connector;
   wherein when said primary Luer female connector is configured to mate with a primary Luer male connector having a secondary female section, said secondary male section is at least partially inserted into said secondary female section, wherein said inner fluid flow channel diameter d1 is constant throughout said primary Luer female connector, and wherein a distal end of said secondary male section is located within the void of said primary Luer female connector, the void being defined by an interior bore of said primary Luer female connector.

3. The connector of claim 2, wherein said secondary male section has a length L, which is higher than E max, wherein E max is the maximal distance formed between the top distal part of primary Luer male connector and the deepest point of primary Luer female connector, when primary Luer male connector and primary Luer female connector are mated.

4. The connector of claim 2, wherein said secondary male section comprises at sealing tip on a top portion thereof.

5. The connector of claim 2, wherein said secondary male section comprises a first conducting material, wherein said first conducting material is configured to close a circuit with a second conducting material positioned on said secondary female section when said primary Luer female connector and said primary Luer male connector are correctly placed with respect to one another.

6. The connector of claim 5, wherein said first conducting material comprises electrode strips.

7. The connector of claim 2, for use in a gas analyzing device.

8. The connector of claim 2, wherein said primary Luer female connector comprises threads on an outer part thereof.

9. A Luer connector for use in a respiratory gas sampling and/or delivery tubing systems, the connector comprising:
a primary Luer female connector having a form of a tapered cone, wherein at its deepest point, the tapered cone inverts back into a secondary male section and returns into a void of said primary Luer female connector, wherein said secondary male section comprises an outer wall and an inner wall, said inner wall being non-tapered thereby forming an inner fluid flow channel, of a diameter d1, extending along said secondary male section and along said primary Luer female connector;
wherein when said primary Luer female connector mates with a primary Luer male connector having a secondary female section, said secondary male section is at least partially inserted into said secondary female section,
wherein said inner fluid flow channel diameter d1 is constant throughout said primary Luer male connector and said primary Luer female connector; and
wherein said secondary male section comprises one or more side slits to permit allowance for tolerance.

10. A Luer connector for use in a respiratory gas sampling and/or delivery tubing systems, the connector comprising:
a primary Luer female connector having a form of a tapered cone, wherein at its deepest point, the tapered cone inverts back into a secondary male section and returns into a void of said primary Luer female connector, such that a distal end of said secondary male section is located within the void of said primary Luer female connector, the void being defined by an interior bore of said primary Luer female connector, wherein said secondary male section comprises a second inner fluid flow channel extending along the length thereof and having an internal diameter of approximately d1,
wherein said secondary male section of said primary Luer female connector comprises a first electric material, wherein said first electric material is configured to close a circuit with a second electric material positioned on a primary Luer male connector when said primary Luer female connector and said primary Luer male connector are correctly placed with respect to one another.

11. The connector of claim 10, wherein said secondary male section comprises said first electric material.

12. The connector of claim 10, wherein said first and/or second electric materials comprise a conducting, inductance, capacitance, resistance element or any combination thereof.

13. The connector of claim 10, wherein when said primary Luer female connector and said primary Luer male connector mate with each other, said secondary male section is at least partially inserted into a secondary female section.

14. A Luer connector for use in a respiratory gas sampling and/or delivery tubing systems, the connector comprising:
a primary Luer female connector having a form of a tapered cone, said primary Luer female connector comprising a spring loaded insert inverting back into a void of primary Luer female connector,
wherein said primary Luer female connector comprises a first electric element, wherein said first electric element is configured to close a circuit with a second electric element positioned on a primary Luer male connector when said primary Luer female connector and said primary Luer male connector are correctly placed with respect to one another.

15. The connector of claim 14, wherein said spring loaded insert comprises said first electric material.

16. The connector of claim 14, wherein said first and/or second electric materials comprise a conducting, inductance, capacitance, resistance element or any combination thereof.

17. The connector of claim 14, wherein when said primary Luer female connector and said primary Luer male connector mate with each other, said spring loaded insert is at least partially inserted into said secondary female section.

* * * * *